(12) United States Patent
Mook et al.

(10) Patent No.: US 11,987,579 B2
(45) Date of Patent: May 21, 2024

(54) NICLOSAMIDE ANALOGUES AND THERAPEUTIC USE THEREOF

(71) Applicant: Duke University, Durham, NC (US)

(72) Inventors: Robert A. Mook, Chapel Hill, NC (US); Wei Chen, Chapel Hill, NC (US); Jiangbo Wang, Durham, NC (US); Xiu-Rong Ren, Durham, NC (US); Herbert Kim Lyerly, Chapel Hill, NC (US)

(73) Assignee: Duke University, Durham, NC (US)

( * ) Notice: Subject to any disclaimer, the term of this patent is extended or adjusted under 35 U.S.C. 154(b) by 658 days.

(21) Appl. No.: 17/263,769

(22) PCT Filed: Jul. 30, 2019

(86) PCT No.: PCT/US2019/044184
§ 371 (c)(1),
(2) Date: Jan. 27, 2021

(87) PCT Pub. No.: WO2020/028392
PCT Pub. Date: Feb. 6, 2020

(65) Prior Publication Data
US 2021/0179615 A1      Jun. 17, 2021

Related U.S. Application Data

(60) Provisional application No. 62/725,006, filed on Aug. 30, 2018, provisional application No. 62/712,103, filed on Jul. 30, 2018.

(51) Int. Cl.
| | |
|---|---|
| *C07D 471/04* | (2006.01) |
| *A61K 45/06* | (2006.01) |
| *A61P 35/04* | (2006.01) |
| *C07D 235/10* | (2006.01) |
| *C07D 249/18* | (2006.01) |

(52) U.S. Cl.
CPC ............ *C07D 471/04* (2013.01); *A61K 45/06* (2013.01); *A61P 35/04* (2018.01); *C07D 235/10* (2013.01); *C07D 249/18* (2013.01)

(58) Field of Classification Search
CPC .. C07D 471/04; C07D 235/10; C07D 249/18; A61K 45/06; A61P 35/04; A61P 35/00
See application file for complete search history.

(56) References Cited

U.S. PATENT DOCUMENTS

| | | | |
|---|---|---|---|
| 2,777,855 A * | 1/1957 | Scalera | C07D 249/18 548/185 |
| 6,469,058 B1 | 10/2002 | Grove et al. | |
| 10,189,797 B2 | 1/2019 | Chen et al. | |
| 10,562,864 B2 | 2/2020 | Chen et al. | |
| 2011/0124637 A1 | 5/2011 | Vu et al. | |
| 2015/0174086 A1 | 6/2015 | Scheffler et al. | |
| 2016/0333009 A1 * | 11/2016 | Bartlett | C07D 403/12 |
| 2017/0190675 A1 | 7/2017 | Chen et al. | |
| 2018/0015153 A1 | 1/2018 | Tang et al. | |

FOREIGN PATENT DOCUMENTS

| | | | |
|---|---|---|---|
| WO | WO-9710219 A1 * | 3/1997 | ........... C07D 231/12 |
| WO | WO 2016/210289 A1 | 12/2016 | |
| WO | WO 2017/201313 A1 | 11/2017 | |

OTHER PUBLICATIONS

Anastas et al., "WNT signalling pathways as therapeutic targets in cancer," Nature Reviews Cancer, 2012, 13(1): 11-26.
Andrews et al., "The biology and toxicology of molluscicides, Bayluscide," Pharmac Ther, 1983, 19(2): 245-295.
Arend et al., "Inhibition of Wnt/β-catenin pathway by niclosamide: a therapeutic target for ovarian cancer," Gynecologic Oncology, 2014, 134(1): 112-120.
Arend et al., "Niclosamide and its analogs are potent inhibitors of Wnt/β-catenin, mTOR and STAT3 signaling in ovarian cancer," Oncotarget, 2016, 7(52): 86803-86815.
Banker et al., "Modern Pharmaceutics," 1979, Marcel Dekker, Inc., New York, chapters 9 and 10.
Barker et al., "Mining the Wnt pathway for cancer therapeutics, " Nature Reviews Drug Discovery, 2006, 5(12): 997-1014.
Blank et al., "PD-L1/B7H-1 Inhibits the Effector Phase of Tumor Rejection by T Cell Receptor (TCR) Transgenic CD8+ T Cells," Cancer Research, 2004, 64(3): 1140-1145.
Burns, "McCutcheon's vol. 1: Emulsifiers & Detergents," North American ed., 1994, MC Publishing Co., Glen Rock, pp. 236-239.
Cancer Genome Atlas Network, "Comprehensive molecular characterization of human colon and rectal cancer," Nature, 2012, 487(7407): 330-337.
Chang et al., "Pharmacokinetics of anti-SARS-CoV agent niclosamide and its analogs in rats," Journal of Food and Drug Analysis, Yaowu Shipin Fenxi, 2006, 1(4): 329-333.
Chen et al., "Dishevelled 2 recruits β-arrestin 2 to mediate Wnt5A-stimulated endocytosis of Frizzled 4," Science, 2003, 301(5638): 1391-1394.
Chen et al., "Niclosamide: Beyond an antihelminthic drug," Cellular Signalling, 2018, 41: 89-96.
Chen et al., "The anti-helminthic niclosamide inhibits Wnt/Frizzled1 signaling," Biochemistry, 2009, 48(43): 10267-10274.
Clevers et al., "Wnt/β-catenin signaling and disease," Cell, 2012, 149(6): 1192-1205.
DiMeo et al., "A novel lung metastasis signature links Wnt signaling with cancer cell self-renewal and epithelial-mesenchymal transition in basal-like breast cancer," Cancer Research, 2009, 69(13): 5364-5373.

(Continued)

*Primary Examiner* — Eric Olson
*Assistant Examiner* — Samuel L Galster
(74) *Attorney, Agent, or Firm* — Michael Best & Friedrich LLP

(57) ABSTRACT

Described are niclosamide analogue compounds, pharmaceutical compositions thereof, and method of using the corner pounds and compositions for treating a disease associated with dysregulation of the Wnt/Frizzled signaling pathway, such as cancer, fatty liver, antibiotic resistance, and viral infection. The disclosed compounds and compositions may also be used for modulating mitochondrial function and for treating certain non-cancer diseases and/or diorders, such as diabetes, fibrotic disease, primary sclerosing cholangitis.

20 Claims, 9 Drawing Sheets

(56) References Cited

OTHER PUBLICATIONS

Frayha et al., "The mechanisms of action of antiprotozoal and anthelmintic drugs in man," General Pharmacology, 1997, 28(2): 273-299.
Gennaro et al., "Remington's Pharmaceutical Sciences," 15th ed., 1975, Mack Publishing Co., Easton, pp. 335-337.
Gooyit et al., "Reprofiled anthelmintics abate hypervirulent stationary-phase Clostridium difficile," Sci Rep 2016, 6: 33642.
Guo, et al., "Enantioselective addition of diethylzinc to benzaldehyde catalyzed by chiral titanate complexes with helical ligands," Tetrahedron, 1997, 53(12): 4145-4158.
Hamanaka et al., "Mitochondrial reactive oxygen species promote epidermal differentiation and hair follicle development," Science Signaling, 2013, 6(261): ra8.
Howe et al., "Wnt signaling and breast cancer," Cancer Biology and Therapy, 2004, 3(1): 36-41.
Huang et al., "Niclosamide induces apoptosis in human rheumatoid arthritis fibroblast-like synoviocytes," Int. Immunopharmacol., 2016, 31: 45-49.
IUPAC, "Rules for the Nomenclature of Organic Chemistry, Section E: Stereochemistry," Pure Appl. Chem., 1976, 45(1): 13-30.
Iwai et al., "Involvement of PD-L1 on tumor cells in the escape from host immune system and tumor immunotherapy by PD-L1 blockade," PNAS, 2002, 99(19): 12293-12297.
Li et al., "Differential abundance of CK1α provides selectivity for pharmacological CK1α activators to target WNT-dependent tumors," Science Signaling, 2017, 10(485): eaak9916.
Li et al., "Multi-targeted therapy of cancer by niclosamide: A new application for an old drug," Cancer Lett, 2014, 349(1): 8-14.
Li et al., "Niclosamide Overcomes Acquired Resistance to Erlotinib through Suppression of STAT3 in Non-Small Cell Lung Cancer," Mol Cancer Ther, 2013, 12(10): 2200-2212.
Li et al., "SRI36160 is a specific inhibitor of Wnt/β-catenin signaling in human pancreatic and colorectal cancer cells," Cancer Lett, 2017, 389: 41-48.
Liang et al., "Inhibitory effects of niclosamide on inflammation and migration of fibroblast-like synoviocytes from patients with rheumatoid arthritis," Inflammation Res, 2016, 64: 225-233.
Liu et al., "Niclosamide inhibits androgen receptor variants expression and overcomes enzalutamide resistance in castration-resistant prostate cancer," Clinical Cancer Research, 2014, 20(12): 3198-3210.
Lu et al., "Activation of the mTOR Pathway by Oxaliplatin in the Treatment of Colorectal Cancer Liver Metastasis," PLoS One, 2017, 12(1): e0169439.
Lu et al., "Niclosamide Suppresses Cancer Cell Growth By Inducing Wnt Co-Receptor LRP6 Degradation and Inhibiting the Wnt/β-Catenin Pathway," PLoS One, 2011, 6(12): e29290.
McCutcheon's vol. 1, Emulsifiers & Detergents, 1994, North American Edition, pp. 236-239.
Meireles et al., "Discovery of modulators of protein-protein interactions: current approaches and limitations," Curr Top Med Chem, 2011, 11(3): 248-257.
Minde et al., "Large Extent of Disorder in Adenomatous Polyposis Coli Offers a Strategy to Guard Wnt Signalling against Point Mutations," PLoS One, 2013, 8(10): e77257.
Mook et al., "Benzimidazole inhibitors from the Niclosamide chemotype inhibit Wnt/β-catenin signaling with selectivity over effects on ATP homeostasis," Bioorg Med Chem, 2017, 25(6): 1804-1816.
Mook et al., "Small molecule modulators of Wnt/β-catenin signaling," Bioorg Med Chem, 2013, 23(7): 2187-2191.
Mook Jr. et al., "Structure-activity studies of Wnt/β-catenin inhibition in the Niclosamide chemotype: Identification of derivatives with improved drug exposure," Bioorganic Medicinal Chemistry, 2015, 23(17): 5829-5838.
Niu et al., "An in silico protocol for identifying potential poly(ADP-ribose)polymerase-1 (PARP-1) inhibitors from chemical databases," New Journal of Chemistry, 2015, 39: 1060-1066.

Nusse et al., "Wnt/β-Catenin Signaling, Disease, and Emerging Therapeutic Modalities," Cell, 2017, 169(6): 985-999.
Ohigashi et al., "Clinical significance of programmed death-1 ligand-1 and programmed death-1 ligand-2 expression in human esophageal cancer," Clinical Cancer Research, 2005, 11(8): 2947-2953.
Osada et al., "Antihelminth compound niclosamide downregulates Wnt signaling and elicits antitumor responses in tumors with activating APC mutations," Cancer Research, 2011, 71(12): 4172-4182.
Pearson et al., "Nicllosamide therapy for tapeworm infections," Annals of the Internal Medicine, 1985, 102: 550-551.
Porichis et al., "Role of PD-1 in HIV pathogenesis and as target for therapy," Current HIV/AIDS Reports, 2012, 9(1): 81-90.
Pubchem CID 44536361, Create Date Jan. 5, 2010, 6 pages.
Pubchem CID 54044347, Create Date Dec. 4, 2011, 7 pages.
Rajamuthiah et al., "Repurposing Salicylanilide Anthelmintic Drugs to Combat Drug Resistant *Staphylococcus aureus*," PLoS One, 2015, 10(4): e0124595.
Rasmussen et al., "Wnt Signaling and Its Impact on Mitochondrial and Cell Cycle Dynamics in Pluripotent Stem Cells," Genes, 2018, 9(2): 109, 24 pages.
Roesch et al., "Overcoming intrinsic multidrug resistance in melanoma by blocking the mitochondrial respiratory chain of slow-cycling JARID1B(high) cells," Cancer Cell, 2013, 23(6): 811-825.
Sack et al., "Novel Effect of Antihelminthic Niclosamide on S100A4-Mediated Metastatic Progression in Colon Cancer," Journal of the National Cancer Institute, 2011, 103(13): 1018-1036.
Said et al., "Programmed death-1-induced interleukin-10 production by monocytes impairs CD4+ T cell activation during HIV infection.," Nature Medicine, 2010, 16(4): 452-459.
Sebio et al., "The potential of targeting Wnt/β-catenin in colon cancer," Expert Opinion on Therapeutic Targets, 2014, 18(6): 611-615.
Senkowski et al., "Three-Dimensional Cell Culture-Based Screening Identifies the Anthelmintic Drug Nitazoxanide as a Candidate for Treatment of Colorectal Cancer," Mol Cancer Ther, 2014, 14(6): 1504-1516.
Shikata et al., "Mitochondrial uncoupler exerts a synthetic lethal effect against β-catenin mutant tumor cells," Cancer Sci, 2017, 108(4): 772-784.
Swan, "The pharmacology of halogenated salicylanilides and their anthelmintic use in animals : review article," Journal of the South African Veterinary Association, 1999, 70(2) 61-70.
Tabatabai et al., "Targeting the Wnt Pathway in Cancer: A Review of Novel Therapeutics," Target Oncol, 2017, 12(5): 623-641.
Taketo, "Shutting down Wnt signal-activated cancer," Nature Genetics, 2004, 36: 320-322.
Tao et al., "Niclosamide ethanolamine-induced mild mitochondrial uncoupling improves diabetic symptoms in mice," Nature Medicine, 2014, 20,(11):1263-1269.
Terada, "Uncouplers of oxidative phosphorylation," Environmental Health Perspectives, 1990, 87: 213-218.
Topalian et al., "Safety, Activity, and Immune Correlates of Anti-PD-1 Antibody in Cancer," The New England Journal of Medicine, 2012, 366(26): 2443-54.
Tran et al., "Modulating the wnt signaling pathway with small molecules," Protein Sci, 2017, 26(4): 650-661.
Velu et al., "Role of PD-1 co-inhibitory pathway in HIV infection and potential therapeutic options," Retrovirology, 2015, 12:14.
Wang et al., "Antiviral activities of niclosamide and nitazoxanide against chikungunya virus entry and transmission," Antiviral Research, 2016, 135: 81-90.
Weinbach et al., "Mechanism of action of reagents that uncouple oxidative phosphorylation," Nature, 1969, 221: 1016-1018.
Weinberg et al., "Targeting mitochondria metabolism for cancer therapy," Nat Chem Biol, 2015, 11(1): 9-15.
Wenninger et al., "C.T.F.A. Cosmetic Ingredient Handbook," 2nd ed., 1992, Cosmetic, Toiletry, and Fragrance Association, Washington D.C., pp. 587-592.
WHO, The Selection and Use of Essential Medicines World Health Organization Geneva, 2007, 188 pages.

(56) References Cited

OTHER PUBLICATIONS

Williamson et al., "Salicylanilides: A New Group of Active Uncouplers of Oxidative Phosphorylation," Science, 1967, 158(3809): 1694-1695.
Wolf, "Is reliance on mitochondrial respiration a "chink in the armor" of therapy-resistant cancer?," Cancer Cell, 2014, 26(6): 788-795.
Xu et al., "Identification of small-molecule inhibitors of Zika virus infection and induced neural cell death via a drug repurposing screen," Nature Medicine, 2016, 22(10): 1101-1107.
Yang et al., "The evolving roles of canonical WNT signaling in stem cells and tumorigenesis: implications in targeted cancer therapies," Lab Invest, 2016, 96: 116-136.
Zhan et al., "Wnt signaling in cancer," Oncogene, 2017, 36\(11); 1461-1473.
Zhang et al., "Induction of mitochondrial dysfunction as a strategy for targeting tumour cells in metabolically compromised microenvironments," Nat Commun, 2014, 5: 3295.
Zhang et al., "Targeting mitochondrial biogenesis to overcome drug resistance to MAPK inhibitors," The Journal of Clinical Investigation, 2016, 126(5): 1834-1856.
International Search Report and Written Opinion for Application No. PCT/US2019/044184 dated Sep. 30, 2019 (26 pages).

\* cited by examiner

NICLOSAMIDE ANALOGUES AND THERAPEUTIC USE THEREOF

CROSS-REFERENCE TO RELATED APPLICATIONS

This patent application is the U.S. national stage entry, under 35 U.S.C. § 371, of International Application Number PCT/US2019/044184, filed Jul. 30, 2019, which claims the benefit of and priority to U.S. Provisional Application No. 62/712,103, filed on Jul. 30, 2018 and U.S. Provisional Application No. 62/725,006, filed on Aug. 30, 2018, the entire contents of each of which are hereby incorporated by reference, and priority to which is hereby claimed.

STATEMENT OF GOVERNMENT INTEREST

This invention was made with government support under Grant numbers R01-CA172570 awarded by the National Cancer Institute (NCI) and 5K12-CA100639 awarded by the National Cancer Institute (NCI). The government has certain rights in the invention.

TECHNICAL FIELD

The present disclosure relates to niclosamide analogue compounds, compositions, and methods for treating Wnt/Frizzled related diseases and/or disorders, such as cancer.

BACKGROUND

Wnt proteins are secreted glycoproteins that bind and activate the seven transmembrane receptor Frizzled and single transmembrane receptors LRP5/6. Wnt binding to Frizzled and LRP5/6 results in activation of cytosolic proteins Dishevelled (Dvl), leading to internalization of the Frizzled receptor. Downstream signaling events resulting from Wnt binding include the stabilization and translocation of cytosolic β-catenin proteins into the nucleus, activation of the transcription factor LEF/TCF and transcription of Wnt/β-catenin target genes.

The Wnt signaling pathway plays a key role in tissue development and homeostasis and is dysregulated in many diseases including cancer. For example, in colorectal cancer (CRC) more than 80% of all sporadic and hereditary cancers show hyperactivation of the pathway due to mutations in the adenomatous polyposis cob (APC) or the β-catenin gene. Given the importance of the Wnt signaling activity underlying tumor formation and metastasis, therapies against the Wnt signaling pathway are highly sought after.

Niclosamide, a drug approved by the FDA for use as an anthelminthic therapy, promotes Frizzled internalization. Studies have found that niclosamide downregulates Dishevelled and β-catenin and inhibits colon cancer cell growth in vitro and in vivo. Whereas the pharmacokinetic properties of niclosamide are appropriate for use in the gut as an anthelmintic agent, its low solubility, low bioavailability and poor pharmacokinetic profile results in low plasma exposure when dosed orally.

Accordingly, there exists a need for modification of, or a synthetic analogue of, niclosamide that is well tolerated in vivo, and possesses drug-like properties that are appropriate for oral dosing to subjects in need of anticancer therapy.

SUMMARY OF THE INVENTION

In one aspect, the present disclosure relates to the use of a compound of formula (I'), or a pharmaceutically acceptable salt thereof, for the treatment of a disease associated with dysregulation of the Wnt/Frizzled signaling pathway,

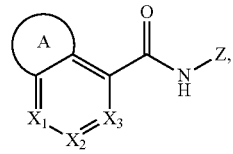

wherein,

is

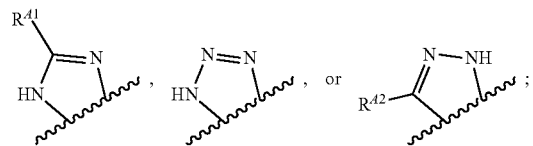

$X_1$ is N or $CR^{x1}$;
$X_2$ is N or $CR^{x2}$;
$X_3$ is N or $CR^{x3}$;
Z is aryl or heteroaryl, wherein the aryl and the heteroaryl are optionally substituted with 1, 2, 3, or 4 $R^Z$;
$R^{A1}$ and $R^{A2}$ are haloalkyl, halogen, oxo, cyano, nitro, —OH, alkoxy, or —C(O)alkyl;
$R^{x1}$, $R^{x2}$, and $R^{x3}$ are independently selected from the group consisting of hydrogen, halogen, nitro, alkyl, cyano, haloalkyl, alkoxyalkyl, heteroalkyl, alkenyl, alkynyl, heterocycle, carboxyl, heterocyclealkyl, —OH, alkoxy, —$OR^4$, —$SR^5$, —$NR^6R^7$, and —$NR^8$—$SO_2$—$R^9$; or $R^{x1}$ and $R^{x2}$ or $R^{x2}$ and $R^{x3}$ together with the carbon atoms they are attached to form a ring;
$R^Z$ at each occurrence is independently selected from the group consisting of halogen, nitro, alkyl, cyano, haloalkyl, alkoxyalkyl, heteroalkyl, alkenyl, alkynyl, heterocycle, carboxyl, heterocyclealkyl, —OH, alkoxy, —$OR^4$, —$SR^3$, —$NR^6R^7$, —$SO_2$—$R^9$, and —$NR^8$—$SO_2$—$R^9$;
$R^4$ is selected from, —C(O)-alkyl, —C(O)-alkenyl, —C(O)-heteroalkyl, —C(O)-heteroaryl, —C(O)-alkoxyalkyl, —C(O)—O-heteroalkyl, —C(O)—O-heteroaryl, —C(O)—O-alkyl, —C(O)—O-alkenyl, and —C(O)—O-alkoxyalkyl;
$R^5$, $R^6$ and $R^7$ are each independently selected from hydrogen, alkyl, —C(O)-alkyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl;
$R^8$ is selected from hydrogen and alkyl, and
$R^9$ is selected from, hydrogen, alkyl, aryl, heteroaryl, arylalkyl, heterocycle and heteroarylalkyl.

In another aspect, the present disclosure relates to a compound of formula (I), or a pharmaceutically acceptable salt thereof,

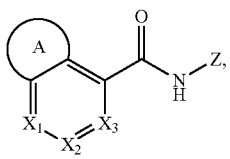

(I)

wherein A, $X_1$, $X_2$, $X_3$, and Z are as defined in formula (I'), provided that if

is

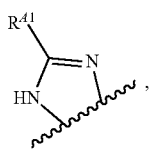

at least one of $X_1$, $X_2$, and $X_3$ is not CH;

provided that Z is not benzo[d]thiazole or substituted benzo[d]thiazole, and provided that the compound is not 6-chloro-2-(trifluoromethyl)-N-(4-(trifluoromethyl)phenyl)-1H-benzo[d]imidazole-4-carboxamide, 2-chloro-N-(3-chloro-4-fluorophenyl)-6,7-difluoro-1H-benzimidazole-4-carboxamide, or N-(3,5-dichloro-4-pyridinyl)-7-methoxy-2-(trifluoromethyl)-1H-benzimidazole-4-carboxamide.

In another aspect, disclosed are pharmaceutical compositions comprising an effective amount of a compound of formula (I) and at least one pharmaceutically acceptable carrier.

In yet another aspect, disclosed is a method of treating a disease associated with dysregulation of the Wnt/Frizzled signaling pathway in a subject in need thereof, the method comprising administering to the subject an effective amount of a compound of formula (I') or formula (I), or a pharmaceutically acceptable salt thereof, provided that, if the disease is cancer, the compound is not 6-chloro-2-(trifluoromethyl)-N-(4-(trifluoromethyl)phenyl)-1H-benzo[d]imidazole-4-carboxamide.

BRIEF DESCRIPTION OF THE DRAWINGS

FIG. 2A show's that DK419 and niclosamideinduce Fzd1-GFP internalization. Fzd1-GFP stable U2OS cells were treated for 6 h at 37° C. with DMSO (i), 12.5 µM niclosamide (ii), or 12.5 µM DK419 (iii). Internalized vesicles are noted with arrowheads. FIG. 2B shows that DK419 and niclosamideinhibit Wnt/β-catenin signaling in TQPFlash assay. HEK293 cells stably expressing TQPFlash luciferase and Renilla luciferase reporters were treated with Wnt3A-conditioned medium in the presence of DMSO or compounds from 0.04 to 10 µM. The TOPFlash reporter activity of Wnt3A with DMSO treatment was set as 100%. DK419 $IC_{50}$=0.19±0.08 µM; niclosamide $IC_{50}$=0.45±0.14 µM. Data were fit using GraphPad Prism (mean±SEM, n=3). FIG. 2C show's reduction of Wnt/β-catenin target gene protein levels in HCT116, SW-480 and CRC240 cells by DK4I9 or niclosamide. Cells were treated with DMSO or compounds in DMSO at 5 µM for 18 h. Cytosolic fractions and whole cell lysate were analyzed by western blot, β-actin was used as a loading control.

FIG. 3A show's oxygen consumption rate in CCD841Co colonic cells in the presence of 1 µM niclosamide, 1 µM DK419, or DMSO, as measured using a Seahorse XFp Analyzer. Compound addition noted by arrows. Control compounds 1 µM Oligomycin, 1 µM FCCP, and 0.5 µM Rotenone & Antimycin added at the end of the experiment (arrows). Data are mean±SD, N=2. OCR was measured under basal conditions. FIG. 3B shows representative results of CCD841Co colonic cells treated for 2 hours with DK419 or niclosamide, in which the whole cell lysate was analyzed by Western blot, β-actin was used as a loading control.

FIG. 5A shows tumor volume. FIG. 5B shows body weight. Data represent means±SEM. N=3. *p<0.05 (Two-way ANOVA analysis between vehicle vs niclosamide or DK419 treatment). FIG. 5C shows tumors collected from mice evaluated by Western Blot for levels of Wnt pathway target gene proteins Axin2, Survivin and c-Myc. β-actin used as a loading control. FIG. 5D show's the levels of Wnt target gene proteins from Western blots in FIG. 5C as quantified by normalizing to β-actin, which were found to decrease in the samples treated with DK419 as compared to vehicle control. Data represent mean±SEM. N=3. *p<0.05 by a two-tailed Student's t test of DK419 treated group compared to the control group.

DETAILED DESCRIPTION

Figure 1:
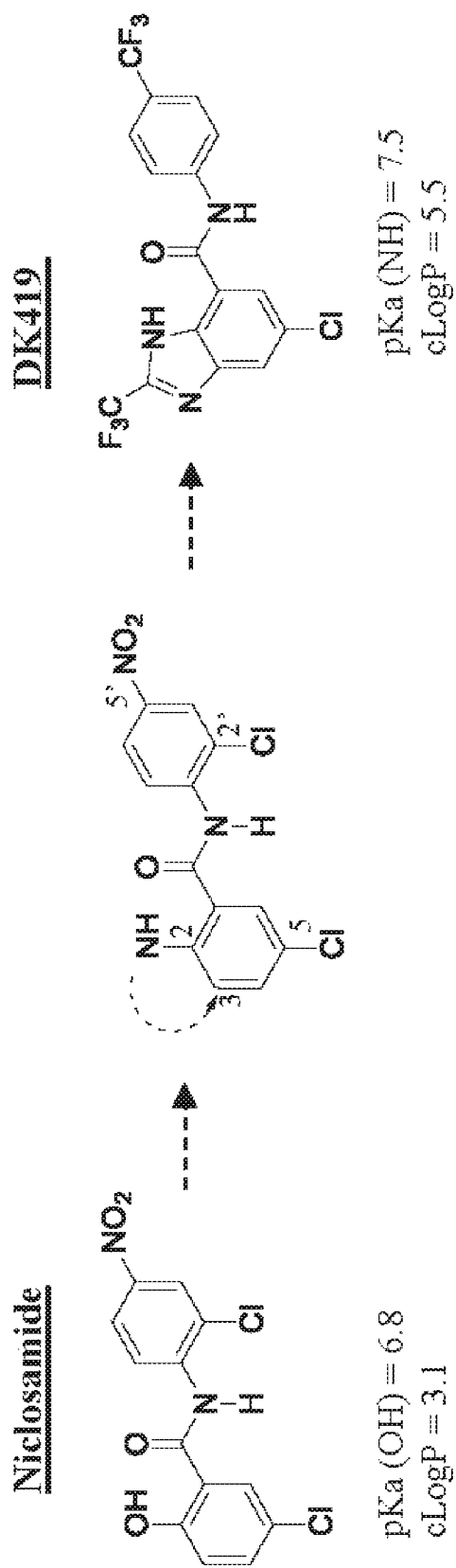
FIG. 1 show's a representative inhibitor design. The hydrogen-bond donating phenolic OH group of niclosamide is replaced with a NH group in a heterocyclic imidazole ring and the pKa adjusted by inserting a $CF_3$ substituent. The $NO_2$ group of niclosamide is replaced with a —$CF_3$ group based on previous SAR studies. Molecular properties are calculated in Maestro (Schrodinger, LLC).

Disclosed herein are methods of treating a disease associated with dysregulation of the Wnt/Frizzled signaling pathway. The Wnt/Frizzled signaling pathway has been implicated in a number of different diseases and/or disorders such as cancer and metabolic diseases such as type II diabetes. Based on the multifunctional bioactivity of the Wnt inhibitor niclosamide, this pathway may also be implicated in other diseases and/or disorders such as lupus, bacterial and viral infection, nonalcoholic steatohepatitis (NASH) and nonalcoholic fatty liver disease (NAFLD). Treatment of the disease associated with dysregulation of the Wnt/Frizzled signaling pathway may be accomplished by use of the compounds disclosed herein. Accordingly, the compounds disclosed herein are inhibitors of the Wnt/Frizzled signaling pathway.

As part of an effort to discover Wnt inhibitors with improved potency, selectivity and pharmacokinetic properties for clinical evaluation, compounds were synthesized and evaluated. Surprisingly, it was found that certain derivatives of niclosamide possess a significantly improved pharmacokinetic profile over niclosamide when dosed orally to mice.

In a particular aspect, the present disclosure relates to niclosamide analog compounds with improved pharmacokinetic properties that maintain the multifunctional drug activity of niclosamide for clinical evaluation, for example, compounds containing a 1H-benzo[d]imidazole-4-carboxamide substructure. Molecular design for the compounds disclosed herein may be carried out using the structure-activity relationships (SAR) of the niclosamide salicylanilide chemotype. Similar to niclosamide, these compounds may inhibit Wnt/β-catenin signaling, alter cellular oxygen consumption rate, and induce production of pAMPK. Moreover, these compounds may inhibit the growth of CRC tumor cells in vitro, have good plasma exposure when dosed orally, and inhibit the growth of patient derived CRC240 tumor explants in mice dosed orally. Thus, the niclosamide analogue compounds disclosed herein may have multifunctional activity and improved pharmacokinetic properties, and may be used to treat diseases associated with dysregulation of the Wnt/Frizzled signaling pathway, such as cancer, fatty liver, antibiotic resistance, bacterial infection (including those caused by drug resistant bacteria), viral infection, diabetes, fibrotic disease, and primary sclerosing cholangitis.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below-, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). Tire modifier "about" should also be considered as disclosing the range defined by the absolute values of the two endpoints. For example, the expression "from, about 2 to about 4" also discloses the range "from 2 to 4." Tire term "about" may refer to plus or minus 10% of the indicated number. For example, "about 10%" may indicate a range of 9% to 11%, and "about 1" may mean from 0.9-1.1. Other meanings of "about" may be apparent from, the context, such as rounding off, so, for example "about 1" may also mean from 0.5 to 1.4.

A "disease associated with dysregulation of the Wnt/Frizzled signaling pathway," as used herein, is a disease in which the Wnt/Frizzled signaling pathway is dysregulated. Certain exemplary Wnt/Frizzled-related diseases include, but are not limited to, cardiovascular disease, neoplasm, obesity, osteoporosis, neuron degeneration, cancer, diabetes, and disorders in wound healing and tissue repair. The Wnt/Frizzled signaling pathway may be considered dysregulated when, for example, diseased tissue and/or cells comprise at least one of: increased levels of β-catenin; increased LEF/TCF-mediated transcription; increased levels of one or more Wnt proteins, including, but not limited to, Wnt3A; increased levels of Frizzled; and/or increased levels of Dishevelled; as compared to normal tissue and/or cells. As used herein, the term "tissue" includes all biological tissues, including, but not limited to, organ tissue, tumor tissue, skin, blood, etc.

The term "effective amount," as used herein, refers to a dosage of the compounds or compositions effective for eliciting a desired effect. This term as used herein may also refer to an amount effective at bringing about a desired in vivo effect in an animal, preferably, a human, such as treatment of a disease.

The term "treatment", as used herein in the context of treating a disease or condition, pertains generally to treatment and therapy, whether of a human or an animal (e.g. in veterinary applications), in which a desired therapeutic effect is achieved. For example, treatment includes prophylaxis and can ameliorate or remedy the condition, disease, or symptom, or treatment can inhibit the progress of the condition or disease (e.g., reduce the rate of disease/symptom progression or halt the rate of disease/symptom progression).

Definitions of specific functional groups and chemical terms are described in more detail below. For purposes of this disclosure, the chemical elements are identified in accordance with the Periodic Table of the Elements, CAS version. Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 20 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, w-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkoxyalkyl" as used herein, refers to an alkoxy group, as defined herein, appended to the parent molecular moiety through an alkylene group, as defined herein.

The term "arylalkyl" as used herein, refers to an aryl group, as defined herein, appended to the parent molecular moiety through an alkylene group, as defined herein.

The term "heteroarylalkyl" as used herein, refers to a heteroaryl group, as defined herein, appended to the parent molecular moiety through an alkylene group, as defined herein.

The term "heterocyclealkyl" as used herein, refers to a heterocycle group, as defined herein, appended to the parent molecular moiety through an alkylene group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkoxy" as used herein, means at least one alkyl group, as defined herein, is appended to the parent molecular moiety through an oxygen atom. Representative examples of alkoxy include, but are not limited to, methoxy, ethoxy, and isopropoxy.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "carboxyl" as used herein, means a carboxylic acid, or —COOH.

The term "haloalkyl" as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" as used herein, means Cl, Br, I, or F.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, thiazolyl, and quinolinyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$] decane), and oxa-adamantane (2-oxatricyclo[3.3.1.1$^{3,7}$]

decane). The monocyclic, bicyclic, and tricyclic heterocycles are connected to the parent molecular moiety through any carbon atom or any nitrogen atom contained within the rings, and can be unsubstituted or substituted.

The term "heteroalkyl," as used herein, means an alkyl group, as defined herein, in which at least one of the carbons of the alkyl group is replaced with a heteroatom, such as oxygen, nitrogen, and sulfur.

The term "hydroxyl" or "hydroxy" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

Tire term "substituents" refers to a group "substituted" on an aryl, heteroaryl, phenyl or pyridinyl group at any atom of that group. Any atom can be substituted.

The term "parenterally," as used herein, refers to modes of administration which include intravenous, intramuscular, intraperitoneal, intrasternal, subcutaneous and intrarticular injection and infusion.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated

2. COMPOUNDS

In one aspect, the present disclosure relates to a compound of formula (I'), or a pharmaceutically acceptable salt thereof,

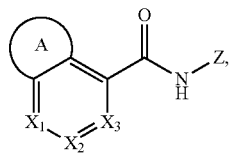
(I')

wherein,

is

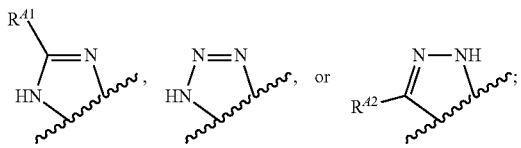

$X_1$ is N or $CR^{x1}$;
$X_2$ is N or $CR^{x2}$;
$X_3$ is N or $CR^{x3}$;
Z is aryl or heteroaryl, wherein the aryl and the heteroaryl are optionally substituted with 1, 2, 3, or 4 $R^z$;
$R^{A1}$ and $R^{A2}$ are haloalkyl, halogen, oxo, cyano, nitro, —OH, alkoxy, or —C(O)alkyl;
$R^{x1}$, $R^{x2}$, and $R^{x3}$ are independently selected from the group consisting of hydrogen, halogen, nitro, alkyl, cyano, haloalkyl, alkoxyalkyl, heteroalkyl, alkenyl, alkynyl, heterocycle, carboxyl, heterocyclealkyl, —OH, alkoxy, —$OR^4$, —$SR^5$, —$NR^6R^7$, and —$NR^8$—$SO_2$—$R^9$; or $R^{x1}$ and $R^{x2}$ or $R^{x2}$ and $R^{x3}$ together with the carbon atoms they are attached to form a ring;
$R^z$ at each occurrence is independently selected from the group consisting of halogen, nitro, alkyl, cyano, haloalkyl, alkoxyalkyl, heteroalkyl, alkenyl, alkynyl, heterocycle, carboxyl, heterocyclealkyl, —OH, alkoxy, —$OR^4$, —$SR^5$, —$NR^6R^7$, —$SO_2$—$R^9$, and —$NR^8$—$SO_2$—$R^9$;
$R^4$ is selected from —C(O)-alkyl, —C(O)-alkenyl, —C(O)-heteroalkyl, —C(O)-heteroaryl, —C(O)-alkoxyalkyl, —C(O)—O-heteroalkyl, —C(O)—O-heteroaryl, —C(O)—O-alkyl, —C(O)—O-alkenyl, and —C(O)—O-alkoxyalkyl;
$R^5$, $R^6$ and $R^7$ are each independently selected from hydrogen, alkyl, —C(O)-alkyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl;
$R^8$ is selected from hydrogen and alkyl; and
$R^9$ is selected from hydrogen, alkyl, aryl, heteroaryl, arylalkyl, heterocycle and heteroarylalkyl.

In a particular embodiment, the compounds of formula (I') have of a structure of formula (I), or a pharmaceutically acceptable salt thereof,

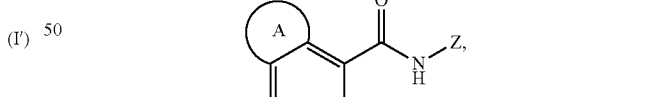
(I)

wherein A, $X_1$, $X_2$, $X_3$, and Z are as defined in formula (I'),
provided that if

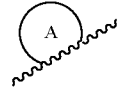

is

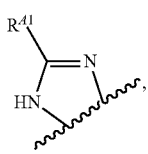

at least one of $X_1$, $X_2$, and $X_3$ is not CH;

provided that Z is not benzo[d]thiazole or substituted benzo[d]thiazole, and provided that the compound is not 6-chloro-2-(trifluoromethyl)-N-(4-(trifluoromethyl)phenyl)-1H-benzo[d]imidazole-4-carboxamide, 2-chloro-N-(3-chloro-4-fluorophenyl)-6,7-difluoro-1H-benzimidazole-4-carboxamide, or N-(3,5-dichloro-4-pyridinyl)-7-methoxy-2-(trifluoromethyl)-1H-benzimidazole-4-carboxamide.

In some embodiments of formula (I') or formula (I), or a pharmaceutically acceptable salt thereof,

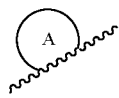

is

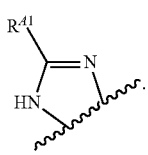

In some embodiments of formula (I') or formula (I), or a pharmaceutically acceptable salt thereof, $X_1$ is $CR^{x1}$, $X_2$ is $CR^{x2}$, and $X_3$ is $CR^{x3}$.

In some embodiments of formula (I') or formula (I), or a pharmaceutically acceptable salt thereof, one of $X_1$, $X_2$, and $X_3$ is N, or two of $X_1$, $X_2$, and $X_3$ are N.

In some embodiments of formula (I') or formula (I), or a pharmaceutically acceptable salt thereof, $R^{41}$ is $C_{1-4}$ haloalkyl.

In some embodiments of formula (I') or formula (I), or a pharmaceutically acceptable salt thereof, $R^{41}$ is —$CF_3$.

In some embodiments of formula (I') or formula (I), or a pharmaceutically acceptable salt thereof, $X_2$ is $CR^{x2}$, and $R^{x2}$ is hydrogen, halogen, nitro, cyano, or haloalkyl.

In some embodiments of formula (I') or formula (I), or a pharmaceutically acceptable salt thereof, $X_2$ is $CR^{x2}$, and $R^{x2}$ is halogen.

In some embodiments of formula (I') or formula (I), or a pharmaceutically acceptable salt thereof, $X_2$ is N.

In some embodiments of formula (I') or formula (I), or a pharmaceutically acceptable salt thereof, Z is a phenyl optionally substituted with 1, 2, 3, or 4 $R^z$.

In some embodiments of formula (I') or formula (I), or a pharmaceutically acceptable salt thereof, Z is

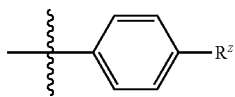

In some embodiments of formula (I') or formula (I), or a pharmaceutically acceptable salt thereof, $R^z$ is $C_{1-4}$alkyl, $C_{1-4}$haloalkyl, $C_{1-4}$alkoxy, halogen, cyano, or nitro.

In some embodiments of formula (I') or formula (I), or a pharmaceutically acceptable salt thereof, $R^z$ is —$CF_3$.

In some embodiments of formula (I') or formula (I), or a pharmaceutically acceptable salt thereof, Z is a monocyclic heteroaryl or a bicyclic heteroaryl.

Representative compounds of formula (I') include, but are not limited to:

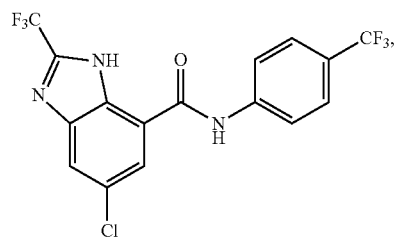 [SMILES: O=C(Nc1ccc(C(F)(F)F)cc1)c1cc(Cl)cc2nc(C(F)(F)F)[nH]c12]

or a pharmaceutically acceptable salt thereof.

Representative compounds of formula formula (I') or formula (I) include, but are not limited to:

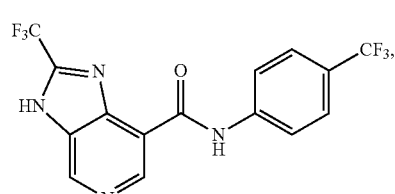

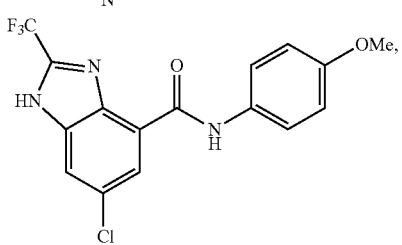

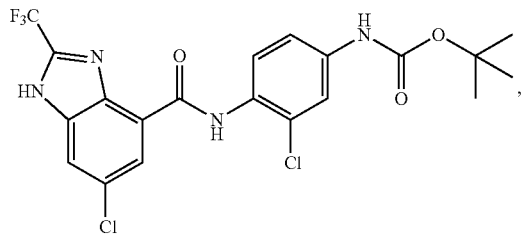

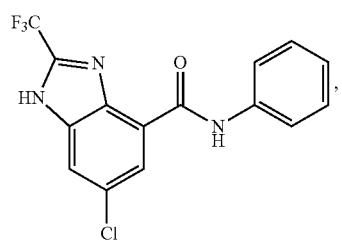

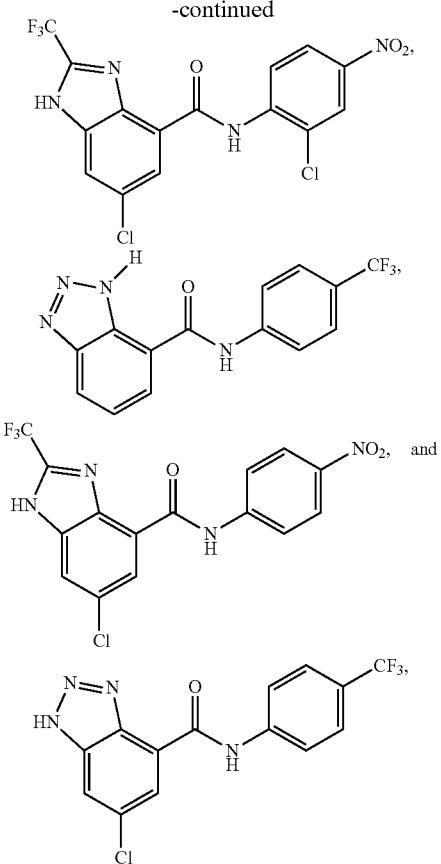

or a pharmaceutically acceptable salt thereof.

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "V" depending on the configuration of substituents around the chiral carbon atom. The terms "R" and "S" used herein as configurations as defined in TUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

Tire present invention also includes an isotopically-labeled compound, which is identical to those recited in the present disclosure, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{35}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of the present disclosure are $^{11}$C, $^{13}$N, $^{15}$O, and $^{18}$F. Isotopically-labeled compounds of the present disclosure can generally be prepared by conventional techniques known to those skilled in the art or by processes analogous to those described in the accompanying Examples using appropriate isotopically-labeled reagent in place of non-isotopically-labeled reagent.

A. Inhibition of Wnt Signaling

The disclosed compounds may act or function as inhibitors of the Wnt/Frizzled signaling pathway. The compounds may promote the anti-proliferation of cancer ceils even in the presence of Wnt/Frizzled signaling dysfunction.

Compounds of the present disclosure can inhibit Wnt-3A-stimulated signaling with an $IC_{50}$ ranging from about 1 nM to about 30 μM. The compounds may have an $IC_{50}$ of about 30 μM, about 29 μM, about 28 μM, about 27 μM, about 26 μM, about 25 μM, about 24 μM, about 23 μM, about 22 μM, about 21 μM, about 20 μM, about 19 μM, about 18 μM, about 17 μM, about 16 μM, about 15 μM, about 14 μM, about 13 μM, about 12 μM, about 11 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, or about 1 nM. Compounds of the present disclosure can inhibit Wnt-3A-stimulated signaling with an $IC_{50}$ of less than 30 μM, less than 29 μM, less than 28 μM, less than 27 μM, less than 26 μM, less than 25 μM, less than 24 μM, less than 23 μM, less than 22 μM, less than 21 μM, less than 20 μM, less than 19 μM, less than 18 μM, less than 17 μM, less than 16 μM, less than 15 μM, less than 14 μM, less than 13 μM, less than 12 μM, less than 11 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methane sulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. General Synthesis

Compounds of formula (I') or formula (I) may be prepared by synthetic processes or by metabolic processes. Preparation of the compounds by metabolic processes includes those occurring in the human or animal body (in vivo) or processes occurring in vitro.

In some embodiments, compounds of formula (I') or formula (I) can be synthesized as shown in the Examples herein.

Employing analogous synthetic methods and the syntheses provided in the Examples, tire remaining compounds of the disclosure may be obtained.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub, Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the shirting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to tire synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. PHARMACEUTICAL COMPOSITIONS

The disclosed compounds may be incorporated into pharmaceutical compositions suitable for administration to a subject (such as a patient, which may be a human or non-human).

The pharmaceutical compositions may include a "therapeutically effective amount" or a "prophylactic-ally effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual, A therapeutically effective amount is also one in which any toxic or detrimental effects of a compound of the invention are outweighed by the therapeutically beneficial effects. A "prophylactically effective amount" refers to an amount effective, at dosages and for period s of time necessary, to achieve the desired prophylactic result. Typically, since a prophylactic dose is used hi subjects prior to or at an earlier stage of disease, the prophylactically effective amount will be less than the therapeutically effective amount.

For example, a therapeutically effective amount of a compound of the present disclosure, may be about 1 mg/kg to about 1000 mg/kg, about 5 mg/kg to about 950 mg/kg, about 10 mg/kg to about 900 mg/kg, about 15 mg/kg to about 850 mg/kg, about 2.0 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, tire compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A, Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp, 236-239, The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active compound and 50% to 99.99% of one or more earners. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic-acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. Tire coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the tike. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compound s include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound, and a carrier. Tire earner of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modem Pharmaceutics, Chapters 9 and 10, Banker & Rhodes, eds. (1979); Lieberman et ah, Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the earner includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, earners for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, ail of winch are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. Tire amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HC-1 or NaOH in amounts sufficient to adjust the pH of a topical pharmaceutical composition.

4. METHODS OF TREATMENT

The Wnt signaling pathway is critical for stem cell development and the proper growth and maintenance of tissues. Dysregulation of this pathway plays an important role in many diseases, particularly cancer. In colorectal cancer (CRC), more than 93% of tumors had alteration in this pathway, ~80% of which were mutations in the Adenomatous polyposis coli (APC) or β-catenin genes that result in hyperactivation of Wnt signaling.

Mechanistic studies have revealed key signaling molecules in the Wnt pathway. In the canonical Wnt pathway, signaling activity is initiated by secreted Wnt protein ligands binding to the seven transmembrane receptor Frizzled and the single transmembrane receptors LRP5/6, resulting in activation of cytosolic Dishevelled (Dvl) proteins, internalization of the Frizzled receptor, and stabilization and translocation of cytosolic β-catenin proteins into the nucleus. Cytosolic β-catenin levels are controlled by a destruction complex consisting of Axin, APC, and two serine-threonine protein kinases, CK1α/δ and GSK3α/β. In CRC, most of the mutations observed in this pathway result in an increase in nuclear β-catenin protein and activation of its target genes. Overall, the Wnt signaling pathway consists of a series of intracellular protein-protein interactions, for which traditional drug discovery approaches have been difficult. To date, no drugs have been approved that specifically target the pathway.

It has been confirmed that the anthelmintic drug niclosamide inhibits Wnt/β-catenin signaling. Niclosamide is a salicylic acid derivative that belongs to the salicylanilide class of anthelmintic agents. It was approved by the FDA in 1982 for use in humans to treat tapeworm infections. Niclosamide has protonophore activity and has been shown to uncouple oxidative phosphorylation. Structurally, niclosamide contains an aryl β-hydroxy carbonyl pharmacophore element that is common in natural products and drugs that encompass a broad range of biological activity. Since its discovery, niclosamide has been shown to have a number of important biological activities that indicate it is a multifunctional drug.

Niclosamide's multi-functional activity has generated considerable interest in its use to treat cancer, rheumatoid arthritis, diabetes, and bacterial and viral infections. There have been clinical trials that evaluate niclosamide's ability to treat cancer (NCT02687009, NCT02519582, NCT02532114, NCT02807805) and rheumatoid arthritis (NCT03160001). As a potential anti-cancer agent. Niclosamide inhibits the growth of cancer cells from multiple tumor types and is active against cancers resistant to other drugs. In addition to inhibition of the Wnt signaling pathway, niclosamide inhibits other key oncogenic signaling pathways such as mTOR, NF-κB, Notch and STAT-3, and has effects on metabolism, including activation of AMPK. Systemic exposure to niclosamide from, an oral dose is low. It is poorly absorbed and is cleared rapidly. Although niclosamide's pharmacokinetic properties are appropriate for use as an anthelmintic agent, its pharmacokinetic and solubility properties may limit its utility in diseases where systemic exposure is required.

As niclosamie analogues, the disclosed compounds and compositions may be used in methods for treatment of Wnt/Frizzled related medical disorders and/or diseases. The methods of treatment may comprise administering to a subject in need of such treatment a composition comprising an effective amount of the compound of formula (I') or formula (I), or a pharmaceutically acceptable salt thereof.

The compositions can be administered to a subject in need thereof to modulate the Wnt/Frizzled signaling pathway for a variety of diverse biological processes. The present disclosure is directed to methods for administering the compositions to inhibit the Wnt/Frizzled signaling pathway, a pathway that plays a key role in tissue development and homeostasis and is dysregulated in many diseases including cancer and metabolic diseases such as type II diabetes.

Based on the multifunctional bioactivity of the Wnt inhibitor niclosamide, this pathway may also be implicated in other diseases and/or disorders such as lupus, bacterial and viral infection, nonalcoholic steatohepatitis (NASH), nonalcoholic fatty liver disease (NAFLD), fibrosis, and primary sclerosing cholangitis. Accordingly, the disclosed compounds and compositions may be administered to a subject for the treatment of cancer, type II diabetes, lupus, bacterial and viral infection, nonalcoholic steatohepatitis (NASH), nonalcoholic fatty liver disease (NAFLD), fibrosis, and primary sclerosing cholangitis.

The compositions may be useful for treating and preventing certain diseases and disorders in humans and animals related to Wnt/Frizzled dysfunction. Treatment or prevention of such diseases and disorders can be effected by inhibiting the Wnt/Frizzled signaling pathway in a subject, by administering a compound or composition of the disclosure, either alone or in combination with another active agent as part of a therapeutic regimen to a subject in need thereof.

In certain embodiments, provided are methods of identifying a subject with a disease associated with dysregulation of the Wnt/Frizzled signaling pathway. The methods may comprise determining the level of at least one protein in a sample from a subject, wherein the protein is involved in the Wnt/Frizzled signaling pathway, and comparing the level of the protein to a standard level. An increased level of the protein may be indicative of a subject having a Wnt/Frizzled-related disease.

The methods of treatment may comprise determining the level of at least one protein in a sample from a subject, wherein the protein is involved in the Wnt/Frizzled signaling pathway, and comparing the level of the protein to a standard level, wherein an increased level of the protein may be indicative of a subject having a a disease associated with dysregulation of the Wnt/Frizzled signaling pathway, and further administering to the subject an inhibitor of the Wnt/Frizzled signaling pathway.

a. Cancer

Inhibition of the Wnt/Frizzled signaling pathway can lead to treatment and reduction of cancer or tumor growth, and/or reduce metastasis of cancerous or tumor cells. Accordingly, the disclosed compositions can be used in methods that treat and/or prevent cancer or tumors in a subject administered the compound. The method can treat cancer or tumor based growth and can be any type of cancer such as, but not limited to, breast cancer, melanoma, prostate cancer, lung cancer, ovarian cancer, esophageal cancer, glioblastoma, multiple myeloma, mantle cell lymphoma, liver cancer, leukemia, acute myelogenous leukemia, or a combination thereof. The cancer may be at least partially resistant to treatment with niclosamide. The cancer may be resistant to niclosamide. In some embodiments, the compounds disclosed herein may inhibit mTor, NF-kB, Stat3, and/or notch signaling. Such inhibitory' activity' may be useful in the treatment of cancer.

In some embodiments, the administered composition to a subject in need thereof can mediate reduction, clearance or prevention of additional growth of tumor cells by inhibiting the Wnt/Frizzled signaling pathway, thereby reducing growth/proliferation or modifying differentiation of tumor cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

In certain embodiments, a subject in need of treatment for cancer may have at least one inactivating mutation of the Adenomatous Polyposis Coli (APC) gene, winch is related to the Wnt/Frizzled signaling pathway. In certain embodiments, a subject in need of treatment for cancer may have at least one mutation of the β-catenin gene or overexpression of the β-catenin protein, or a combination thereof. In certain embodiments, a subject in need of treatment for cancer may have overexpression of Wnt ligands.

In certain embodiments, determining whether a cancer comprises a dysregulated Wnt/Frizzled signaling pathway may comprise detecting the level of one or more of Wnt, Frizzled, β-catenin, and/or Dishevelled, and comparing the level to normal tissue and/or cells. In certain such embodiments, if the cancer comprises higher levels of Writ, Frizzled, β-catenin and/or Dishevelled as compared to normal tissue and/or cells, the cancer is predicted to respond to treatment with an inhibitor of the Wnt/Frizzled signaling pathway. In certain embodiments, determining whether a cancer comprises a dysregulated Wnt/Frizzled signaling pathway comprises detecting the level of LEF/TCF-mediated transcription as compared to LEF/TCF-mediated transcription in normal tissue and/or cells. In certain such embodiments, if the cancer comprises a higher level of LEF/TCF-mediated transcription as compared to normal tissue and/or cells, the cancer is predicted to respond to treatment with an inhibitor of the Wnt/Frizzled signaling pathway.

A variety of sources (Howe, et al. *Cancer Biology and Therapy* 2004, 5(1), 36-41; Taketo, M. *Nature Genetics* 2004, 36, 320-22; Minde et al. *PLOS ONE* 2013, 5(10), e77257) have reported that activity of the Wnt/Frizzled pathway is involved in the development of benign and malignant breast tumors. Furthermore, its presence is indicated with elevated levels of β-catenin in the nucleus and/or cytoplasm, and increased β-catenin expression is strongly correlated with poor prognosis in breast cancer patients. This accumulation may be due to several factors such as mutations in β-catenin, deficiencies in the β-catenin destruction complex, most frequently by mutations in structurally disordered regions of APC, overexpression of Wnt ligands, loss of inhibitors, and/or decreased activity of regulatory pathways. Breast tumors have also been seen to metastasize due to Wnt involvement in the epithelial-mesenchymal transition (EMT). Investigation of the metastasis of basal-like breast cancer to the lungs has shown that repression of Wnt/β-catenin signaling can prevent EMT, which can inhibit metastasis (DiMeo, et al. *Cancer Research* 2009, 69(13), 5364-5373).

Wnt signaling has also been implicated in the development of other cancers. Changes in CTNNB1 expression, which is the gene that encodes β-catenin, can be measured in not just breast cancer, but also colorectal cancer, melanoma, prostate cancer, lung cancer, and several other cancer types. Increased expression of Wnt ligand-proteins such as Wnt1, Wnt2, and Wnt7A have been observed in the development of glioblastoma, esophageal cancer, and ovarian cancer respectively. Other proteins known to cause multiple types of cancer in the absence of proper functioning include ROR1, ROR2, SFRP4, Wnt5A, WIFI, and those of the TCF/LEF family (Anastas, et al. *Nature Reviews Cancer* 2012, 13 (1), 11-26).

Accordingly, the foregoing firmly implicate the Wnt/Frizzled signaling pathway in the biology of a variety of cancer types and distinguish it as a cancer target.

b. Modulation of Mitochondrial Function/Other Non-cancer Indications

The disclosed compounds and compositions may be used in methods for modulating mitochondrial function, for example, by causing the uncoupling of mitochondrial oxidative phosphorylation. The methods of modulating mitochondrial function may comprise administering to a subject in need of such treatment a composition comprising an effective amount of the compound of formula (I') or formula (I), or a pharmaceutically acceptable salt thereof.

In some embodiments, the disclosed compounds or compositions may cause uncoupling oxidative phosphorylation and induce AMPK phosphorylation. In some embodiments, the disclosed compounds or compositions may cause oxygen consumption rate to increase in a subject. In some embodiments, tire disclosed compounds or compositions may inhibit the spare respiratory capacity of mitochondria in a subject.

In some embodiments, the disclosed compounds or compositions may be used for modulating mitochondrial function at a concentration of about 30 µM, about 29 µM, about 28 µM, about 27 µM, about 26 µM, about 25 µM, about 24 µM, about 23 µM, about 22 µM, about 21 µM, about 20 µM, about 19 µM, about 18 µM, about 17 µM, about 16 µM, about 15 µM, about 14 µM, about 13 µM, about 12 µM, about 11 µM, about 10 µM, about 9 µM, about 8 µM, about 7 µM, about 6 µM, about 5 µM, about 4 µM, about 3 µM, about 2 µM, about 1 µM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, or about 1 nM. Compounds of tire present disclosure can modulate mitochondrial function at a concentration of less than 30 µM, less than 29 µM, less than 28 µM, less than 27 µM, less than 26 µM, less than 25 µM, less than 24 µM, less than 23 µM, less than 22 µM, less than 21 µM, less than 20 µM, less than 19 µM, less than 18 µM, less than 17 µM, less than 16 µM, less than 15 µM, less than 14 µM, less than 13 µM, less than 12 µM, less than 11 µM, less than 10 µM, less than 9 µM, less than 8 µM, less than 7 µM, less than 6 µM, less than 5 µM, less than 4 µM, less than 3 µM, less than 2 µM, less than 1 µM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

The compounds and compositions may be administered to a subject in need thereof to modulate the mitochondrial function in a variety of non-cancer indications and diseases and/or disorders, such as fatty liver, antibiotic resistance, viral infection, diabetes, fibrotic disease, and primary sclerosing cholangitis. Accordingly, the disclosed compounds and compositions may be administered to a subject for the treatment of fatty liver, antibiotic resistance, bacterial infection, viral infection, diabetes, fibrotic disease, and primary sclerosing cholangitis.

In some embodiments, the compounds and compositions disclosed herein may be administered to a subject having a bacterial infection, such as an infection caused by drug resistant bacteria. In some embodiments, the compounds and compositions disclosed herein may be administered to a subject having a viral infection. The infection may be caused by, for example, Zika virus, Ebola virus, or Dengue virus. Accordingly, the disclosed compounds and compositions may be administered to a subject for the treatment of a viral infection caused by Zika virus, Ebola virus, or Dengue virus.

c. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arable, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g, Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form, of an aqueous, lipid, oily or other kind of solution or suspension or even administered in the form of liposomes or nano-suspensions.

d. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present disclosure. The above combinations include combinations of a compound of the present disclosure not only with one other active compound, but also with two or more other active compounds. For example, the compound of the disclosure can be combined with a variety of anti-cancer drags and chemotherapeutics.

The disclosed compounds can be combined with the following, but not limited to, actinomycins, alkylating agents, anthracyclines, antifolates, antiestrogen agents, antimetabolites, anti-androgens, antimicrotubule agents, aromatase inhibitors, bleomycins, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multidrug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, and vitamin D3 analogs. Specific anti-cancer or chemotherapeutic agents that may be combined with a disclosed compound include actinoinycin D, AG13736, alisertib, 17-allylamino-17-demethoxygeldanamycin, altretamine, 9-aminocamptothecin, N-(4-(3-amino-1H-indazol-4-yl)phenyl}-N'-(2-fluoro-5-methylphenyl) urea, N-(4-(4-aminothieno[2,3-d]pyrimidin-5-yl)phenyl}-N'-(2-fluoro-5-(trifluoromethyl)phenyl)urea, anastozole, AP-23573, asparaginase, axitinib, azacitidine, bevacizumab, bicalutamide, bevacizumab, bleomycin a2, bleomycin b2, bortezemib, busulfan, campathecins, carboplatin, carmustine (BCNU), CB1093, CHOP (C: Cytoxan® (cyclophosphamide); H: Adriamycin® (hydroxydoxorubicin); O: Vincristine (Oncovin®)); P: predmsone), chlorambucil, CHIR258, cilengitide, cisplatin, CNF-101, CNF-1001, CNF-2024, CP547632, crisnatol, cytarabine, cyclophosphamide, cytosine arabinoside, daunorubicin, dabrafenib, dacarbazine, dactinornycin, dasatinib, daunorubicin, deferoxamine, demethoxyhypocrellin A, depsipeptide, 17-dimethylaminoethylamino-17-demethoxygeldanamycin, docetaxel, doxifluridine, doxorubicin, EB 1089, enzastaurin, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fiudarabine, flutamide, gefitinib, geldanamycin, gemcitabine, goserelin, N-(2-(4-hydroxyanilino}-3-pyridinyl}-4-methoxybenzenesulfonamide, hydroxyurea, idarubicin, ifosfamide, imatinab, interferon-a, interferon-y, IPI-504, irinotecan, KH 1060, lapatinib, leucovorin calcium, LAQ824, leuprolide acetate, letrozole, lomustine (CCNU), melphalan, mercaptopurine, methotrexate, 1-methyl-4-phenylpyridinium, MG132, mitoxantrone, mitozolomide, MLN4924, MLN518, MS-275, mycophenolic acid, nedaplatin, oprelvekin, oxahplatin, paclitaxel, PD98059, pazopanib, peplomvcin, phtalocyanine, pirarubicin, plicamycin, procarbazine, PTK787, PU24FC1, PU3, radicicol, raloxifene, rapamycin, ratitrexed, pheuretinide, ribavirin, rituximab (Rituxin®), satraplatin, sorafenib, staurosporine, suberoylanilide hydroxamic acid, sunitinib, tamoxifen, taxol, temozolomide, temsirolimus, teniposide, thapsigargin, thioguanine, thrombospondin-1, tiazofurin, topotecan, trapoxin, treosulfan, trichostatin A, trimetrexate, triplatin tetranitrate, trofosfamide, tumor necrosis factor, valproic acid, vemurafenib, VER49009, verapamil, vertoporfin, vinblastine, vincristine, vindesine, vinorelbine vitamin D3, VX-680, zactima, ZK-EPO, zorubicin, trastuzumab, cetuximab, lambrolizumab, nivolumab or any combination thereof.

In some embodiments, the disclosed compounds may be combined with a mTor inhibitor, such as sirolimus, everrolimus, or temsirolimus.

The disclosed compounds may be included in kits comprising the compound (e.g., one or more disclosed compound), a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

5. EXAMPLES

Material and Methods. c Log P and pKa values were calculated using Maestro (Schrodinger, LLC). c Log P values are QP Log P (octanol/water) calculated in Qikprops. The pKa values were calculated in water solvent in Epik (Version 10.3.015, Schrodinger, LLC).

Example 1. Synthesis of Compounds

Molecular design was earned out with an aim to remove substituents in niclosamide's structure associated with its poor PK properties while keeping SAR features associated with inhibition of Wnt signaling and uncoupling of oxidative phosphorylation. In the design, the 2-hydroxy and 4'-nitro substituents known to be sites of metabolism were removed, while at the same time providing a hydrogen bond donating group at the 2-position with a pKa of ~6-7, the ability to hydrogen bond to and delocalize its corresponding conjugate base, and a c log P≥3. Accordingly, the 2-hydroxy group of the salicylic motif was replaced with a heterocyclic NH group and modulated its pKa by the appropriate placement of electron-withdrawing substituents (FIG. 1). In particular, 6-chloro-2-(trifluoromethyl)-N-(4-(trifluoromethyl)phenyl)-1H-benzo[d]imidazole-4-carboxamide (DK419), an imidazole ring substituted with a trifluoromethyl group was used. In the anilide ring, the 4'-nitro group was replaced with a trifluoromethyl group based on previous SAR studies that indicated it was suitable replacement for the nitro group. DK419 has a calculated pKa=7.5 and a calculated Log P (c Log P)=5.5, which met the other design criteria.

DK419 was synthesized in 5 steps starting from, commercially available 2-methyl-6-nitroaniline (Scheme I).

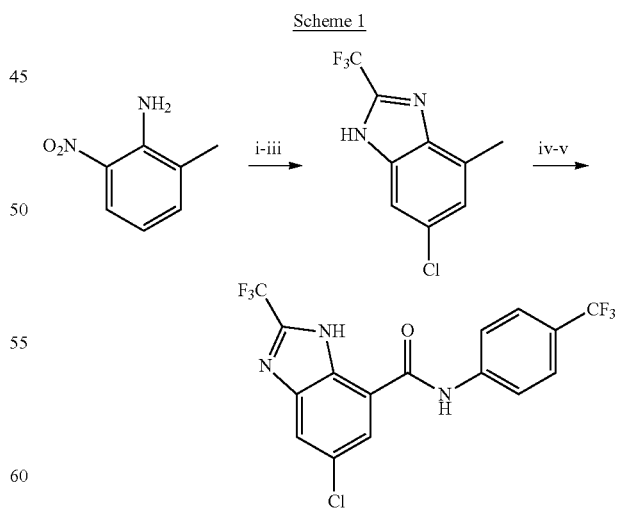

Scheme 1

DK419
i. NCS, AcOH ii. RaNi, $H_2$ iii. TFA iv. KMnO$_4$ v. HATU, 4-trifluoroaniline.

To a 2-necked round-bottom flask equipped with an addition funnel, a thermometer and a magnetic stir bar under an Argon atmosphere was added 12.97 g (85.23 mmol) of 2-methyl-6-nitroaniline and 35 ml glacial acetic acid. The suspension was placed in a pre-heated oil bath at 50° C. to produce a red solution. To the addition funnel was added a suspension of 11.95 g N-chlorosuccinimide (NCS) in ca. 45 mL of acetic acid. Tire NCS suspension was added dropwise over ca. 15 minutes while maintaining the temperature around 55° C. After the addition was complete, the addition funnel was rinsed with acetic acid (ca. 5 mL) and added, A brown homogeneous solution resulted during the course of the reaction. The progress of the reaction was followed by TLC using methylene chloride as the elutant. Upon completion of the reaction, the reaction mixture was cooled to room temperature, poured into 100 mL of water and cooled in an ice bath. The solids were filtered on paper under vacuum, and rinsed with a total of 130 mL of water. The solids were dried in air in the filter funnel under vacuum to yield 13.3 g of 4-chloro-2-methyl-6-nitroaniline as an orange-red solid, $^1$H NMR (400 MHz, DMSO-d6) δ 7.82 id. J=2.2 Hz, 1H), 7.38 (br. s, 1H), 7.23 (br. s., 2H), 2.17 (s, 3H). MS (ESI+) m/z=187 (M+1). This material was used in the subsequent reaction without further purification.

To a round-bottom flask equipped with a Claisen adapter and a magnetic stir bar under an argon atmosphere was added 2.24 g (11.95 mmol) of 4-chloro-2-methyl-6-nitroaniline and 95% ethanol (56 mL). To this mixture was added an aqueous (pH ca. 7-8) suspension of RaNi (ca. 2 g). The reaction flask was evacuated and charged 3 times with hydrogen, and then placed in an oil bath pre-heated to 60-70° C. After 4 h, the reaction was complete by TLC (3% methanol/methylene chloride). Tire flask was evacuated and charged 3-4 times with Argon, and celite was added. The mixture was filtered through celite, rinsed sequentially with ethanol and then water, and the filtrate concentrated in vacuo to a brownish oil. The oil was suspended in water (40 mL) and 2.7 mL of trifluoroacetic acid was added, and the resultant mixture refluxed for 2.5 hr. The reaction mixture was then cooled to room temperature. Sodium bicarbonate was added carefully to adjust the pH to ca. 7-8, and the aqueous reaction mixture extracted 2 times with ethyl acetate. Tire ethyl acetate layers were combined and washed with brine, dried over sodium sulfate, filtered, and concentrated in vacuo to give 6-chloro-4-methyl-2-(trifluoromethyl)-1H-benzo[d]imidazole as a solid. MS (ESI+) m/z=235, 233 (M+1). This material was used in subsequent reaction without further purification.

To a round-bottom flask equipped with a magnetic stir bar, and a thermometer and reflux condenser was added 2.11 g (9 mmol) of 6-chloro-4-methyl-2-(trifluoromethyl)-1H-benzo[d]imidazole and 126 ml of 0.5M NaOH. The reaction mixture was placed at reflux and 7.56 g KMnO4 (44.97 mmol) was added in 5 portions over 4 hours. The reaction mixture was then refluxed for 3 additional hours and removed from the oil bath and cooled to ca 50° C. Celite and sodium metabisulfite was added to the reaction flask, and the mixture filtered hot through celite. The filtrate was cooled in an ice-bath, and HCl added to adjust the pH to 3. The resultant aqueous mixture was extracted 3 times with ethyl acetate, and, the ethyl acetate layers were combined, dried over sodium sulfate, filtered, and concentrated onto a plug of silica gel. The silica gel plug was loaded onto a column of silica gel and eluted with 10-80% methanol in methylene chloride. The desired fractions were combined, heptane was added, and the fractions were concentrated in vacuo to give 0.9 g of 6-chloro-2-(trifluoromethyl)-1H-benzo[d]imidazole-4-carboxylic acid as a white-tan solid. $^1$H NMR (400 MHz, DMSO-d6) δ 8.18 (s, 1H), 7.89 (s, 1H). MS (ESI−) m/z=263, 265 (M−1).

To a dry round-bottomed flask was added 2.16 g (8.17 mmol) of 6-chloro-2-(trifluoromethyl)-1H-benzo[d]imidazole-4-carboxylic acid and 45 mL of dry DMF. To the resultant solution was added a solution of 3.42 g (8.99 mmol) HATU (1-[Bis(dimethylamino)methylene]-1H-1,2,3-triazolo[4,5-b]pyridinium 3-oxid hexafluorophosphate) in a total of 15 mL of dry DMF. The mixture was stirred at room temperature for 40 min, at which time 1.1 mL (1.45 g, 8.99 mmol) of 4-(trifluoromethyl)aniline and 4.3 mL (3.16 g, 24.55 mmol) of Hunig's base was added, lire reaction mixture was stirred at room temperature for 24 hr and monitored by TLC using 3% EtOAc/CH$_2$Cl$_2$-Hexane (1:1). The amber solution was poured into 500 mL of water and the pH adjusted to 3 by the addition of 2N HCl. The resultant white precipitate was stirred for 10 min, filtered, washed with water, and air-dried in the filter funnel. The solids were dissolved in EtOAc, and the solution dried with Na$_2$SO$_4$, and filtered. To the filtrate was added heptane and the solution was concentrated under vacuum on a rotary evaporator to give white solid (3.1 g). The solids were loaded onto ca. 40 mL of silica gel by dissolving the solids in EtOAc, adding heptane, and concentrating under vacuum, and these solids were eluted on a column of ca. 500 mL of silica gel with a gradient of 1-7% EtOAc/CH$_2$Cl$_2$. Pure fractions were set aside, and mixed fractions were re-chromatographed, Pure fractions were combined and concentrated. The solids were dissolved in EtOAc, heptane added to the solution, and concentrated to give 1.7 g (51%) of 6-chloro-2-(trifluoromethyl)-N-(4-(trifluoromethyl)phenyl)-1H-benzo[d]imidazole-4-carboxamide as a white solid. $^1$H NMR (400 MHz, DMSO-d6) δ 11.3 (br s, 1H), 8.05-8.07 (br s, 1H), 7.96 (br d, J=8.00 Hz, 3H), 7.76 (d, J=8.69 Hz, 2H). MS (ESI+) m/z=408, 410 (3:1) (M+1); MS (ESI−) m/z=406, 408 (3:1) (M−1).

The following compounds were synthesized in a manner similar to the synthesis schemes and conditions as described for 6-chloro-2-(trifluoromethyl)-N-(4-(trifluoromethyl)phenyl)-1H-benzo[d]imidazole-4-carboxamide.

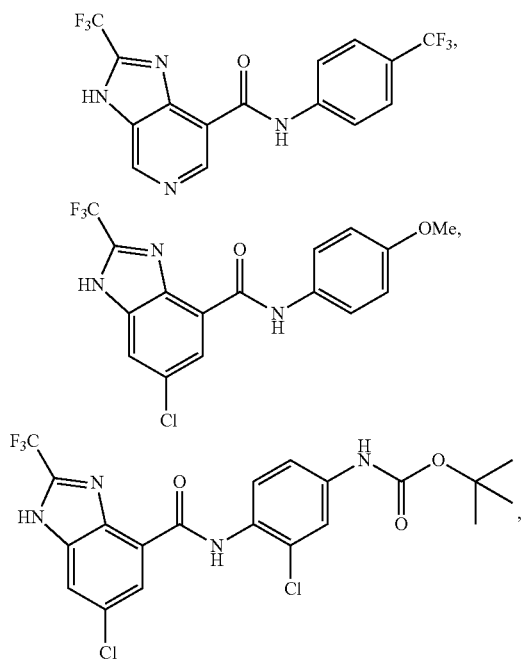

-continued

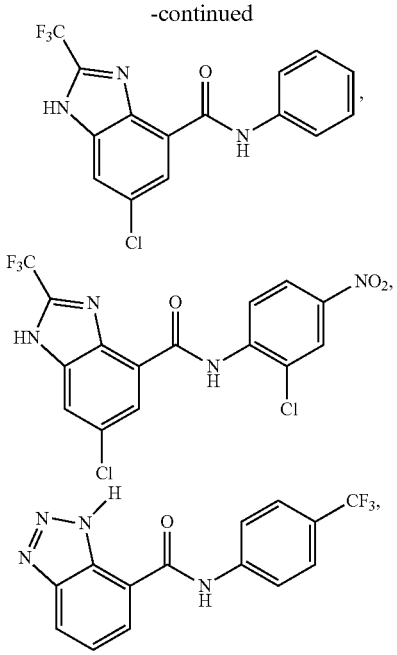

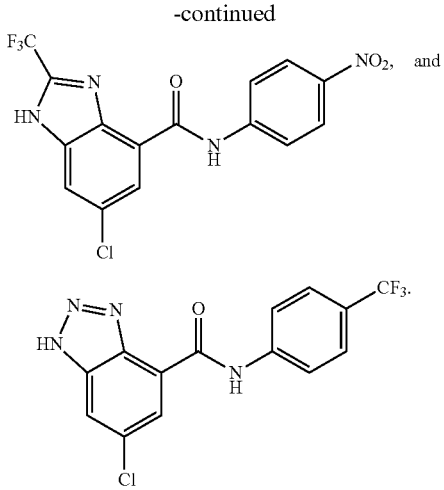

The activities of the above compounds to modulate the Wnt signaling pathway may be tested with experimental processes as described herein (e.g, TopFlash assay).

As non-limiting examples, the syntheses of certain compounds are provided below (Schemes 2 and 3).

| Name | Structure | Chemical formula and molecular weight | Synthesis Route |
|---|---|---|---|
| 6-chloro-N-(4-methoxyphenyl)-2-(trifluoromethyl)-1H-benzo[d]imidazole-4-carboxamide | 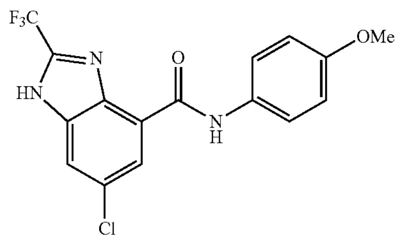 [SMILES: COc1ccc(NC(=O)c2cc(Cl)cc3[nH]c(C(F)(F)F)nc23)cc1] | Chemical Formula: $C_{16}H_{11}ClF_3N_3O_2$ Exact Mass: 369.05 Molecular Weight: 369.73 | Route 2 |
| tert-butyl (3-chloro-4-(6-chloro-2-(trifluoromethyl)-1H-benzo[d]imidazole-4-carboxamido)phenyl)-carbamate | 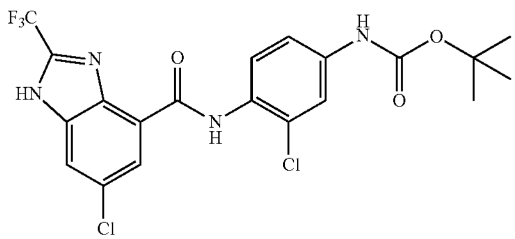 [SMILES: CC(C)(C)OC(=O)Nc1ccc(NC(=O)c2cc(Cl)cc3[nH]c(C(F)(F)F)nc23)c(Cl)c1] | Chemical Formula: $C_{20}H_{17}Cl_2F_3N_4O_3$ Exact Mass: 488.06 Molecular Weight: 489.28 | Route 2 |
| 6-chloro-N-phenyl-2-(trifluoromethyl)-1H-benzo[d]imidazole-4-carboxamide | 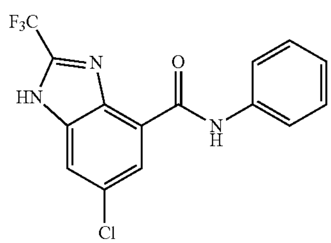 [SMILES: O=C(Nc1ccccc1)c1cc(Cl)cc2[nH]c(C(F)(F)F)nc12] | Chemical Formula: $C_{15}H_9ClF_3N_3O$ Exact Mass: 339.04 Molecular Weight: 339.70 | Route 2 |

| Name | Structure | Chemical formula and molecular weight | Synthesis Route |
|---|---|---|---|
| 6-chloro-N-(2-chloro-4-nitrophenyl)-2-(trifluoromethyl)-1H-benzo[d]imidazole-4-carboxamide | 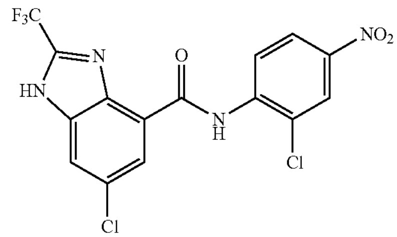 [SMILES: O=C(Nc1ccc([N+](=O)[O-])cc1Cl)c1cc(Cl)cc2[nH]c(C(F)(F)F)nc12] | Chemical Formula: $C_{15}H_7Cl_2F_3N_4O_3$<br>Exact Mass: 417.98<br>Molecular Weight: 419.14 | Route 2 |
| 6-chloro-N-(4-nitrophenyl)-2-(trifluoromethyl)-1H-benzo[d]imidazole-4-carboxamide | 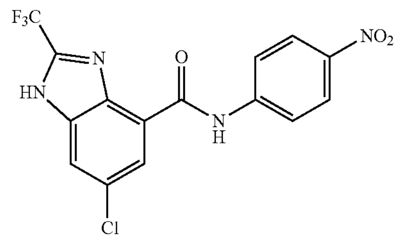 [SMILES: O=C(Nc1ccc([N+](=O)[O-])cc1)c1cc(Cl)cc2[nH]c(C(F)(F)F)nc12] | Chemical Formula: $C_{15}H_8ClF_3N_4O_3$<br>Exact Mass: 384.02<br>Molecular Weight: 384.70 | Route 1 |
| N-(4-nitrophenyl)-2-(trifluoromethyl)-3H-imidazo[4,5-c]pyridine-7-carboxamide | 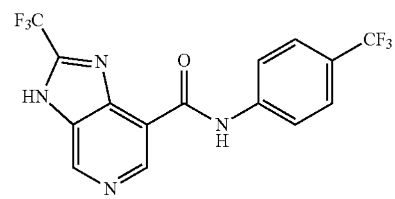 [SMILES: O=C(Nc1ccc(C(F)(F)F)cc1)c1cncc2[nH]c(C(F)(F)F)nc12] | Chemical Formula: $C_{15}H_8F_6N_4O$<br>Exact Mass: 374.06<br>Molecular Weight: 374.25 | See procedure provided |

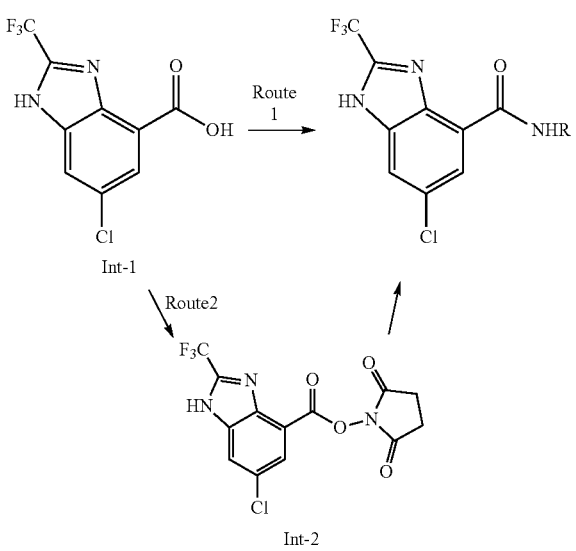

Scheme 2

Route 1

6-chloro-N-(4-nitrophenyl)-2-(trifluoromethyl)-1H-benzo[d]imidazole-4-carboxamide. To a solution of N-[(Dimethylamino)-1H-1,2,3-triazolo-[4,5-b]pyridin-1-ylmethylene]N-methylmethanaminium hexafluorophosphate N-oxide (HATU) (0.089 g, 0.233 mmol) in 0.5 mL dimethylformamide (DMF) was added 6-chloro-2-(trifluoromethyl)-1H-benzo[d]imidazole-4-carboxylic acid (Int-1) (0.056 g, 0.21 mmol) in 0.25 mL DMF. After 25 minutes, 4-nitro aniline (0.032 g, 0.233 mmol) in 1 mL of DMF and 0.11 mL of N,N-Diisopropylethylamine was added. The progress of the reaction was monitored by HPLC/MS. The desired product was isolated by pouring the reaction mixture into water. The resultant suspension was filtered and the solids dissolved in ethyl acetate and extracted 5 times with dilute pH3 aqueous phosphate buffer. The organic layer was dried with sodium sulfate, decanted and concentrated onto a small plug of silica gel. The resultant solids were chromatographed on silica gel with a gradient of 5 to 10% ethyl acetate in 1:1 dichloromethane-hexane. The desired fractions were combined and concentrated. The solids were triturated with dichloromethane and the solids dried under vacuum to give 6-chloro-N-(4-nitrophenyl)-2-(trifluoromethyl)-1H-benzo[d]imidazole-4-carboxamide as a solid, m/z (ESI−): 383, 385 (3:1) [M−1], Route 2

Step 1. Preparation of 2,5-dioxopyrrolidin-1-yl 6-chloro-2-(trifluoromethyl)-1H-benzo[d]imidazole-4-carboxylate (Int-2)

To a solution of 6-chloro-2-(trifluoromethyl)-1H-benzo[d]imidazole-4-carboxylic acid (Int-1) (0.189 g, 0.717 mmol) in 2 mL dry THF was added at room temperature N-hydroxysuccinimide (NHS) (0.092 g, 0.79 mmol) followed by dicyclohexylcarbodiimide (DCC) (0.163 g, 0.79 mmol). The progress of the reaction was monitored by TLC with 10% methanol/dichloromethane. Upon completion, the reaction mixture was concentrated onto a plug of silica gel and the resultant solids chromatographed on silica gel with a gradient of 6-8% ethyl acetate/dichloromethane. The desired fractions were concentrated to yield 98 mg of 2,5-dioxopyrrolidin-1-yl 6-chloro-2-(trifluoromethyl)-1H-benzo[d]imidazole-4-carboxylate (Int-2) as a white solid, m/z (ESI−): 360, 362 (3:1) [M−1].

Step 2. Preparation of Anilide Derivative

Preparation of 6-chloro-N-(4-methoxyphenyl)-2-(trifluoromethyl)-1H-benzo[d]imidazole-4-carboxamide. To a solution of 2,5-dioxopyrrolidin-1-yl 6-chloro-2-(trifluoromethyl)-1H-benzo[d]imidazole-4-carboxylate (Int-2) (9.4 mg, 0.026 mmol) in dry dioxane was added 4-methoxyaniline (11.4 mg, 0.093 mmol) and the progress of the reaction monitored by HPLC/MS. Upon completion, the reaction mixture was concentrated onto a small plug of silica gel and the resultant solids eluted on a column of silica gel with a (4/4/0.2) to (4/4/0.4) gradient of hexane/dichloromethane/ethyl acetate. Tire desired fractions were combined and concentrated to yield 3.5 mg of 6-chloro-N-(4-methoxyphenyl)-2-(trifluoromethyl)-1H-benzo[d]imidazole-4-carboxamide as a solid, m/z (ESI–): 368, 370 (3:1) [M–1].

tert-butyl (3-chloro-4-(6-chloro-2-(trifluoromethyl)-1H-benzo[d]imidazole-4-carboxamido)phenyl)carbamate was similarly prepared using Route 2 by refluxing a solution of Int-2 with tert-butyl (4-amino-3-chlorophenyl)carbamate. The desired compound was isolated by chromatography on silica gel with a gradient of 2-8% ethyl acetate/dichloromethane, m/z (ESI–): 487, 489 (3:1) [M–1].

6-chloro-N-phenyl-2-(trifluoromethyl)-1H-benzo[d]imidazole-4-carboxamide was similarly prepared using Route 2 by heating a solution of Int-2 with aniline at 60° C. lire desired compound was isolated by chromatography on silica gel with a gradient of 2-8% ethyl acetate/dichloromethane, m/z (ESI+): 340, 342 (3:1) [M+1].

6-chloro-N-(2-chloro-4-nitrophenyl)-2-(trifluoromethyl)-1H-benzo[d]imidazole-4-carboxamide was prepared using Route 2 by heating Int-2 with 2-chloro-4-nitroaniline at 190° C. for 25 minutes without solvent. The desired compound was isolated by reverse phase chromatography on C18 using a gradient of 5-98% acetonitrile/water containing 0.2% formic acid buffer. The desired fractions were combined and lyophilized to produce the desired compound as a white solid, m/z (ESI–): 416.9, 418.9 (3:1) [M–1].

Preparation of 2-(trifluoromethyl)-N-(4-(trifluoromethyl)phenyl)-3H-imidazo[4,5-c]pyridine-7-carboxamide To ice-cold sulfuric acid (20 mL) was added as a solid slowly over 5 minutes, 4-aminonicotinic acid (2.57 g, 18.61 mmol). To this mixture, potassium nitrate was added over 1 min, and the resultant suspension warmed to room temperature. The reaction mixture was stirred at room temperature for two and a half hours, and then heated in an 80° C. oil bath for ca. 2 hours. The reaction mixture was then cooled to room temperature and absolute ethanol (40 mL) was added over 10-15 minutes while providing an ice-bath to prevent the mixture from getting too hot. The resultant suspension was then heated at 60° C. and the progress of the reaction monitored by HPLC/MS. The reaction mixture was then cooled in an ice bath and a solution of 110 mL of acetic acid and 76 g sodium hydroxide was added over 1 min. To this mixture sodium chloride was added and the resultant mixture extracted 3-4 times with ethyl acetate, Tire organic layers were combined and washed with brine, dried with sodium sulfate and filtered. The organic layer was concentrated and the residue diluted with dichloromethane. To this solution was added ca. 30 mL of silica gel and the suspension filtered. The solids were eluted with dichloromethane and then 15% ethyl acetate/dichloromethane. The light yellow filtrate was concentrated and the residue azeotroped 2 times with toluene to give 2 g of ethyl 4-amino-5-nitronicotinate (Int-3) as a semi-solid that was taken on into the next step without further purification.

To a solution of 2 g of ethyl 4-amino-5-nitronicotinate in methanol (10 mL) and tetrahydrofuran (5 mL) under an argon atmosphere was added 10% palladium on charcoal (0,108 g). The resultant dark mixture was evacuated and charged with hydrogen gas 3 times, and then stirred at room temperature under a balloon of hydrogen gas. The progress of the reaction was monitored by HPLC/MS, and upon completion, the reaction mixture was evacuated and charged with argon gas 3 times and filtered through a bed of celite. Heptane was added and the solution concentrated to a brown solid. The solids were dissolved in dichloromethane (10 mL) and trifluoroacetic acid (0.6 mL) was added. The mixture was stirred overnight at room temperature and then heated to reflux for ca 5 hours, cooled to room temperature and toluene added (10 mL). A short-path distillation head was added to the flask and ca. 4 ml of solvent distilled off. The reaction mixture was then refluxed for ca. 20 hours with the progress of the cyclization reaction being monitored by HPLC/MS. Potassium phosphate buffer at pH 5 was added to the reaction flask and the dark mixture and solids extracted with dichloromethane. The solids in the flask ware then extracted, with a freshly prepared aqueous sodium

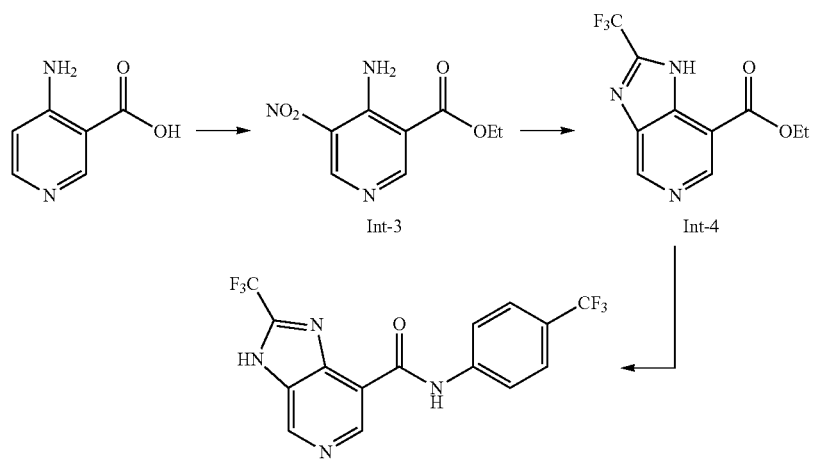

Scheme 3 bicarbonate solution and dichloromethane. The extract solutions were combined, the organic layer separated, and the aqueous layer washed three times with dichloromethane. The organic layers were combined and washed with brine, dried over sodium sulfate and filtered. To the filtrate was added ca. 10 mL of silica gel and the mixture concentrated to a solid. Tire solids were eluted on a column of silica gel with a gradient of 2-3% methanol/dichloromethane. The desired fractions were combined and concentrated to give 0.4 g of ethyl 2-(trifluoromethyl)-1H-imidazo[4,5-c]pyridine-7-carboxylate (Int-4) as an off-white solid, m/z (ESI+): 260 [M+1], m/z (ESI−): 258 [M−1].

To a solution of ethyl 2-(trifluoromethyl)-1H-imidazo[4,5-c]pyridine-7-carboxylate (0.082 g, 0.32 mmol) in 95% ethanol as added 3 mL of 0.5M sodium hydroxide and the resultant mixture heated to reflux for 30 min. Tire reaction mixture was cooled to room temperature and the pH adjusted to 2-3. The mixture was extracted 4 times with dichloromethane and the organic layer concentrated to a solid. The aqueous layer was then concentrated to dryness and the solids combined with the solids obtained from the organic layers. The solids were suspended in a minimal amount of water, and the mixture eluted on a plug of C18 support using a gradient of 50-95% methanol/water. The desired fractions were combined, concentrated, azeotroped 2 times with methanol, and concentrated to give 48 mg of 2-(trifluoromethyl)-1H-imidazo[4,5-c]pyridine-7-carboxylic acid as a white solid, m/z (ESI+): 232 [M+1], m/z (ESI−): 230 [M−1], This material was taken on directly into the next step.

To a solution of 2-(trifluoromethyl)-1H-imidazo[4,5-c]pyridine-7-carboxylic acid (24 mg, 0.104 mmol) in 1 mL of dry DMF was added a solution of N-[(Dimethylamino)-1H-1,2,3-triazolo-[4,5-b]pyridin-1-ylmethylene]-N-methylmethanaminium hexafluorophosphate N-oxide (HATU) (0.043 g, 0.11 mmol) in 0.5 mL DMF. After 25 min, a solution of 4-(trifluoromethyl)aniline (0.018 g, 0.11 mmol) and N,N-Diisopropylethylamine (0.04 g, 0.31 mmol) in DMF was added and the resultant mixture stirred at room temperature. The progress of the reaction was monitored by HPLC/MS, and upon completion, the mixture was poured into dilute aqueous phosphate buffer (pH 4-5) and extracted 3 times with ethyl acetate. The organic layers were combined, washed 5 times with dilute phosphate buffer (pH 4-5), dried with sodium sulfate, decanted and concentrated onto silica gel (3 g). The solids were eluted on a column of silica gel with 2-7% methanol/dichloromethane. The desired fractions were combined and concentrated to give 34 mg of 2-(trifluoromethyl)-N-(4-(trifluoromethyl)phenyl)-3H-imidazo[4,5-c]pyridine-7-carboxamide as solid. HRMS (ESI+) observed 375.0673 [M+1], calculated $C_{15}H_9F_6N_4O$ 375.0675, error=0.7 ppm.

Example 2 Activity Studies

Frizzled Internalization Assay

The Frizzled 1-GFP (Fzd1-GFP) assay was performed following a procedure similar to that previously reported (Chen et al., Biochemistry 2009, 48, 10267). Briefly, U2OS cells stably expressing Fzd1-GFP were plated in con local dishes and incubated at 37° C. with 5% CO2. After 24 hours the cells were treated with 12.5 μM of test compound (dissolved in DMSO) or DMSO alone in media as a control for 6 hours at 37° C. and then fixed with 4% paraformaldehyde. The cells were then examined by microscopy using an LSM 510-Meta confocal microscope (Carl Zeiss, Thornwood, N.Y., USA) equipped with 40× and 100×apo chromat objectives. GFP was excited using a 488-nm argon laser line. Images were processed using the LSM software Image Browser.

TOPFlash Reporter Assay

Wnt-3A conditioned medium was prepared using L WNT-3A cells (ATCC® CRL-2647™) purchased from ATCC, and was obtained using published protocols (http://www.atcc.org/Products/All/CRL-2647.aspx#culturemethod).

HEK293 were stably transfected with p8×TOPFlash, Renilla luciferase plasmid pRL-TK, and pLKO.1. Briefly, stably transfected cells were seeded in 100 μL of cell growth medium (MEM, Sigma, catalog number M4655) supplemented with 10% FBS (Atlanta Biologieals, catalog number S11050), and 1 μg/mL puromycin (Sigma, catalog number P8833), 100 U/mL penicillin-streptomycin (Invitrogen, catalog number 15140122)/well in 96-well plates and incubated in 5% $CO_2$ at 37° C. overnight to 100% confluency. Fifty microliters of Wnt-3A conditioned medium containing the chemical compounds to be tested or DMSO was added to each well. After 6 h treatment, the cell were washed once with PBS and lysed with 55 μL of Passive Lysis Buffer supplied in the Dual-Luciferase Reporter Assay kit (Promega, Catalog number E1960). Twenty-five microliters of cell lysate was used for measuring luciferase activity in a %-well plate reader (FluoStar Optima, BMG Labtech, Chicago, Ill.).

Evaluation of Writ signaling inhibition by Western blot

All cells were plated in 6 well-plates and allowed to attach overnight in a 5% CO2 incubator at 37° C. to reach 50-70 percent confluency. The cells were then treated with the indicated compound for 18 hours. Whole cell lysates were prepared by adding 200 μL 1.5× Laemmli sample buffer. Cytosolic lysates were prepared by treating cells with hypotonic buffer and dispersing cell aggregates by drawing the lysate buffer in and out a syringe equipped with 25G×1 needles. The cytosolic lysate was centrifuged at 15,000 rpm for 120 minutes, 200 μL of cytosol lysate was collected and 67 μL of 4× Laemmli sample buffer was added. Whole cell lysates were subjected to Western blot analysis using antibodies to c-Myc (Santa Cruz Biotechnology, catalog number SC-40), Cyclin D1 (Cell Signaling Technology, catalog number 2978), and Survivin (Cell Signaling Technology, catalog number 2808). Cytosol lysate were subjected to Western blot analysis using antibodies to β-catenin (Santa Cruz Biotechnology SC-7963) and Axin2 (Cell Signaling Technology, catalog number 2151). An antibody to β-actin (Santa Cruz Biotechnology, catalog number SC-47798) was used as a loading control.

Evaluation of Phospho-AMPK Levels by Western Blot 12-well plates were incubated with 250 μL poly-D-lysine solution (Sigma, catalog number P6407) at 10 μg/mL for 30 minutes at room, temperature, the poly-D-lysine solution was removed, and the wells washed twice with 500 μL distilled water. Colonic epithelial CCD841Co cells were cultured in MEM medium plus 1 mM sodium pyruvate (Invitrogen, catalog number 11360070), lx MEM Non-Essential Amino Acids (Gibco catalog number 11140), 10% FBS, and 100 U/ml penicillinstreptomycin. 0.27 million CCD841Co cells per well were plated in culture medium in the poly-Dlysine coated 12-well plates and allowed to attach overnight at 37° C. in a 5% $CO_2$ incubator. The next morning, the media was replaced with DMSO vehicle in cell media, DK419 or niclosamidein DMSO diluted to the indicated concentration with DMEM medium (Sigma, catalog number D5030) supplemented with 2 mM sodium pyruvate and 2 mM L-glutamine (Invitrogen, catalog number 25030081). The medium does not contain glucose. After 30 minutes treatment, the media was removed and the cells were lysed with 120 μL 1×Laemmii sample buffer. Immunoblots of the cell lysates using antibodies to phospho-AMPK (pAMPK) (Cell Signaling Technology, catalog number 2535) and AMPK (Cell Signaling Technology, catalog number 2532) was used to detect phosphorylated AMPK (β-Threonine 172) levels and total AMPK levels, respectively. Antibodies to β-actin were used as loading controls.

Assessment of Oxygen Consumption Rate (OCR)

Colonic epithelial CCD841Co cells were plated in Seahorse XFp 8-well miniplates at 8000 cells/well and allowed to attach overnight at 37° C. in a 5% $CO_2$ incubator. Polarographic analysis of OCR was performed using Seahorse XF Analyzer (Agilent Technologies, Santa Clara, Calif.) and a Seahorse XFp Cell Mito Stress Test Kit (Agilent Technologies, catalog number 103010-100). OCR was measured under basal conditions after the additions of 1 μM niclosamide, 1 μM DK419, or DMSO in media, following the additions of 1 μM Oligomycin, 1 μM FCCP, and 0.5 μM Rotenone & Antimycin A at the times indicated. Data were analyzed by the software Wave (Version 2.3.0.20, Agilent Technologies, Santa Clara, Calif.).

Inhibition of Cell Proliferation by MTS Assay

Colon cancer cell lines SW948, HT-29, HCT116, CRC240, SW480, and DLD-1 were used in the cell proliferation assay. All cell lines, except CRC240, were from ATCC. CRC240, a colorectal cancer patient derived xenograft (PDX) cell line, was obtained from the Hsu lab (Duke University). Generation of CRC240 cell line was previously reported. SW948 cells were cultured in Leibovitz's medium (Gibco, catalog number 21083-027). HT-29 and HCT116 cells were cultured in McCoy's 5A medium (Gibco, catalog number 16600-082). SW480 cells were cultured in MEM medium. CRC240 and DLD-1 cells were cultured in RPMI medium (Gibco, catalog number 11875-093). All media were supplemented with 10% FBS and 100 U/ml penicillin-streptomycin. The cells were plated at 5000 cells per well in 100 μl of culture medium in 96-well plates, and treated with niclosamide or DK419 from concentrations of 0.04 to 10 μM for 72 h, after which time the cells were analyzed by colorimetric MTS assay (Promega, catalog number G3581). $IC_{50}$ values calculated using Graphpad Prism.

Pharmacokinetic Analysis

DK419 was dissolved in 10% N-Methyl pyrrolidinone (Sigma, catalog number 328634) and 90% PEG300 (Sigma, catalog number 20237) at 0.2 mg/mL, and dosed orally to NOD/SCID mice (n=4) at 1 mg/kg. Blood samples (20 μL) were collected serially from tail vein into vials containing 1 μL of 1000 U/mL heparin at the following time-points: pre-dose, 0.25, 0.5, 1, 2, 4, 8, 24, 48, and 72 h after drug administration. After centrifugation at 1300 g for 5 min at room temperature, plasma was separated and stored at −80° C. until the analysis.

Quantification of DK419 in mouse plasma was started by vigorous agitation of 4 μL sample, 10 μL of 20 ng/mL DK4-106-3 (in-house made internal standard analog), 20 μL of water, and 100 μL of ethyl-acetate. After centrifugation at 16,000 g for 5 min at room temperature, 80 μL of organic (upper) layer was dried under nitrogen stream, residue reconstituted with a mixture of 50% mobile phase A (10 mM ammonium acetate, 0.1% formic acid) and 50% mobile phase B (methanol), and 5 μL injected into LC/MS/MS system. Analysis was performed on Shimadzu series 20A LC/Applied Biosystems/SCIEX API 4000 QTrap MS/MS instrument. Column: Agilent Eclipse 4.6×50 ram, 1.8 μm at 50° C. Elution gradient: 0-2 min 50-90% B, 2-2.5 min 90% B, 2.5-2.7 min, 90-50% B; flow 1 min/mL. MS/MS transitions followed: 405.8/218.9 (DK419) and 331.8/311.8 (DK4-106-3; int. std.). Run time: 5 min. Calibration samples were prepared by adding pure DK419 to pooled mouse plasma in 2.4 ng/mL (LLOQ)-1000 ng/mL range and analyzed alongside the PK study samples. The calibration curve was linear (r=0.999).

Xenograft Tumor Studies

The development of CRC240 PDX was previously reported (Lu et al. PLoS One 2017, 12, e0169439). Briefly, CRC240 PDX tissue were wash in PBS and then minced in PBS at 150 mg/mL. 200 μL of the PDX tissue suspension were implanted into the flanks of NOD/SCID mice. When PDX tumor volume reached about 100 $mm^3$, mice were randomized and were orally dosed for 11 days daily byniclosamide, DK419, or the vehicle control (10% 1-methyl-2-pyrrolidmone and 90% PEG300). Niclosamide was suspended in the vehicle at 144 mg/ml and dosed at 72 mg/kg. DK419 was dissolved in the vehicle at 0.2 mg/ml and dosed at 1 mg/kg. Tumor size and body weight were measured at day 0, 4, 8, and 11. The day after the last dose, animals were euthanized and tumor samples were collected and processed for Western blot analysis. Briefly, tumor samples were lysed in RIPA Buffer (Thermofisher Scientific, catalog number 89900). Sample lysates were subjected to Western blot using antibodies to Survivin, c-Myc, and Axin2 as described above. β-actin was used as a loading control.

Results

Figure 2A:
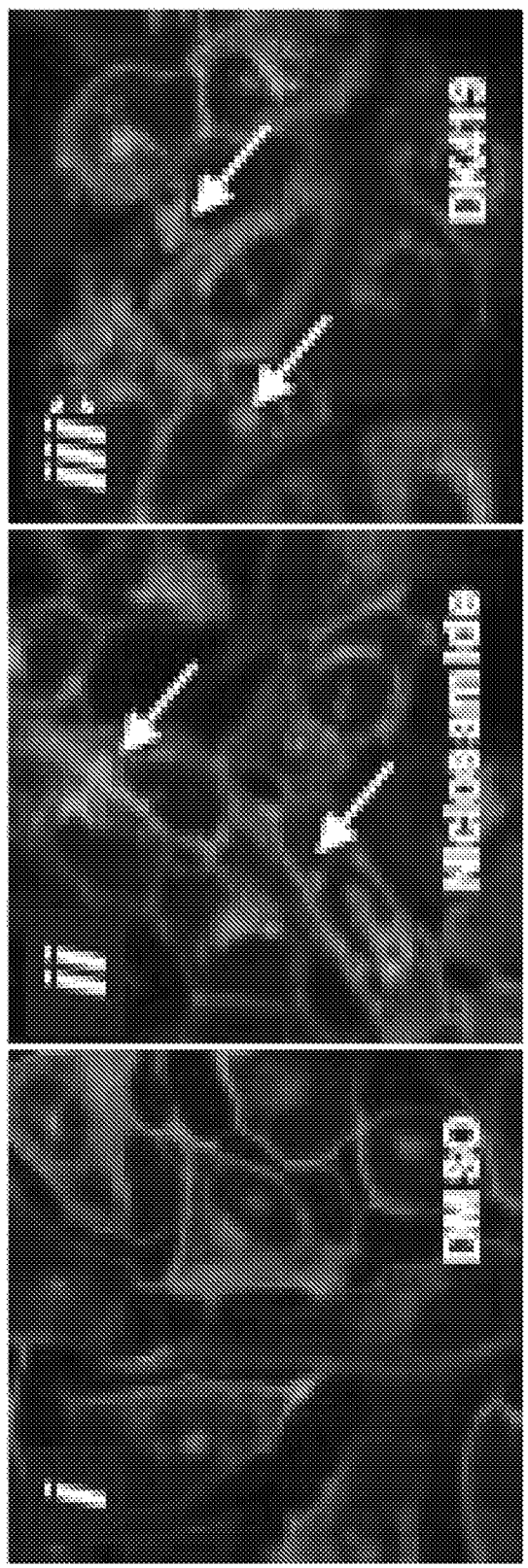
FIGS. 2A-2C shows representative results of inhibition of Wnt/β-catenin signaling by DK419 and niclosamide.
Figure 2B:
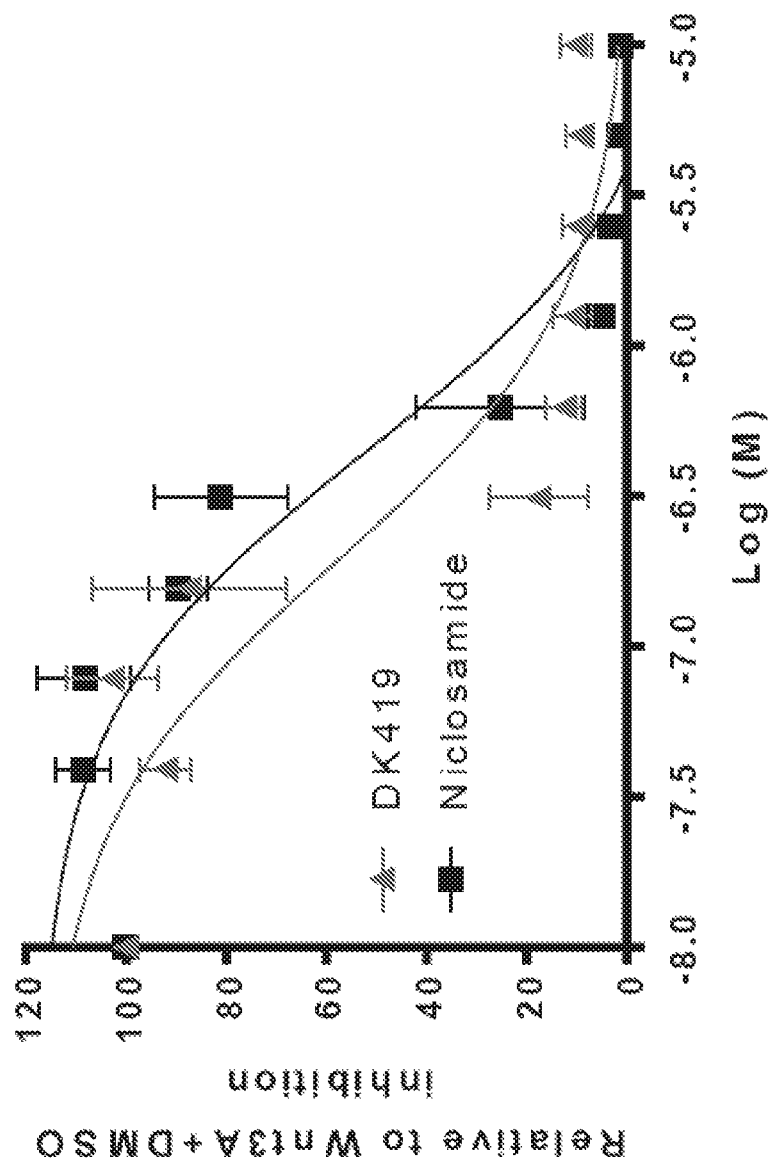
Figure 2C:
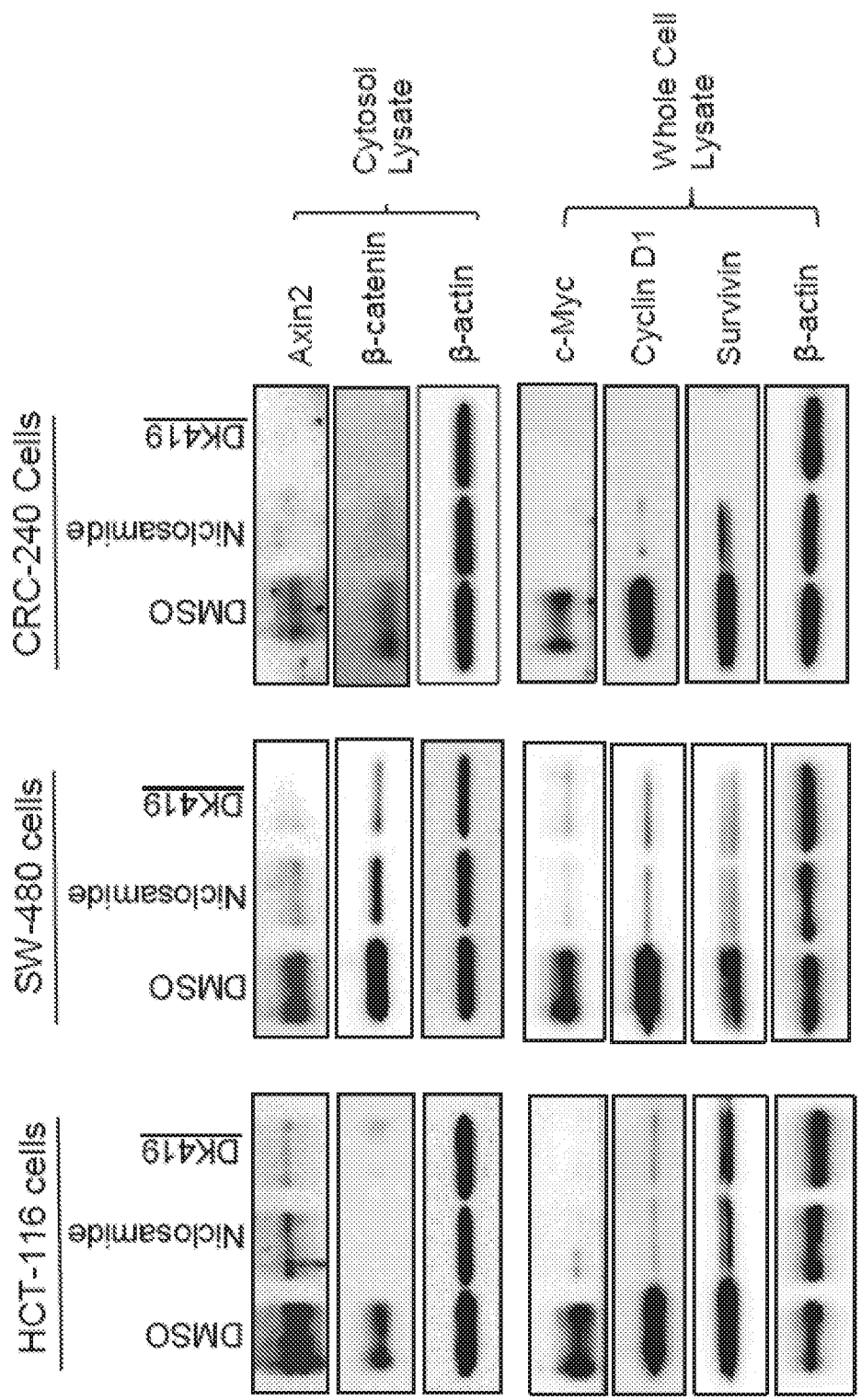

Inhibition of Wnt/β-catenin signaling Niclosamide's activity against the Wnt/β-catenin pathway was first discovered by its ability to internalize the Fzd1 receptor using a novel Fzd1-GFP internalization assay. Similar to previous work that characterized its inhibition of Wnt/β-catenin signaling, DK419 was evaluated in cellular assays to assess internalization of Fzd1-GFP receptor, inhibition of β-catenin gene transcription in the Wnt3A-stimulated TOPFlash reporter assay, and the reduction of Wnt/β-catenin signaling proteins and target genes by Western blot (FIGS. 2A-2C). In the Fzd1-GFP internalization assay, U20S cells stably expressing Fzd1-GFP protein were treated with niclosamideor DK419 at 12.5 μM for 6 hours and compared to control media containing equivalent amounts of DMSO. Frizzled receptor internalization was assessed by the production of a green fluorescent internal puncta using confocal microscopy (FIG. 2A). Both DK419 and niclosamide produced a robust punctate pattern compared to control, indicating that both molecules induce internalization to the receptor. The ability of DK419 to inhibit Wnt/β-catenin gene transcription was next assessed by dose response using the Wnt3A-stimulated β-catenin TOPFlash reporter assay (FIG. 2B). It was found that DK419 inhibited Wnt/β-catenin signaling with an $IC_{50}$ of 0.19±0.08 μM, comparable to niclosamide ($IC_{50}$ of 0.45±0.14 μM). To confirm these results, DK419 and nidosamide were compared in two colorectal cancer cell lines that harbor mutations in the Wnt/β-catenin signaling pathway (HCT-116, β-catenin mutation; SW-480, APC-mutation) and in patient-derived colorectal tumor CRC-240 ceils by Western blot (FIG. 2C). Consistent with the results of the Wnt3A-stimulated TOPFlash assay, both DK419 and niclosamide demonstrated reduced levels of Axin2, (3-catenin, c-Myc, Cyclin D1 and Survivin in all three CRC tumor cell models.

Figure 3A:
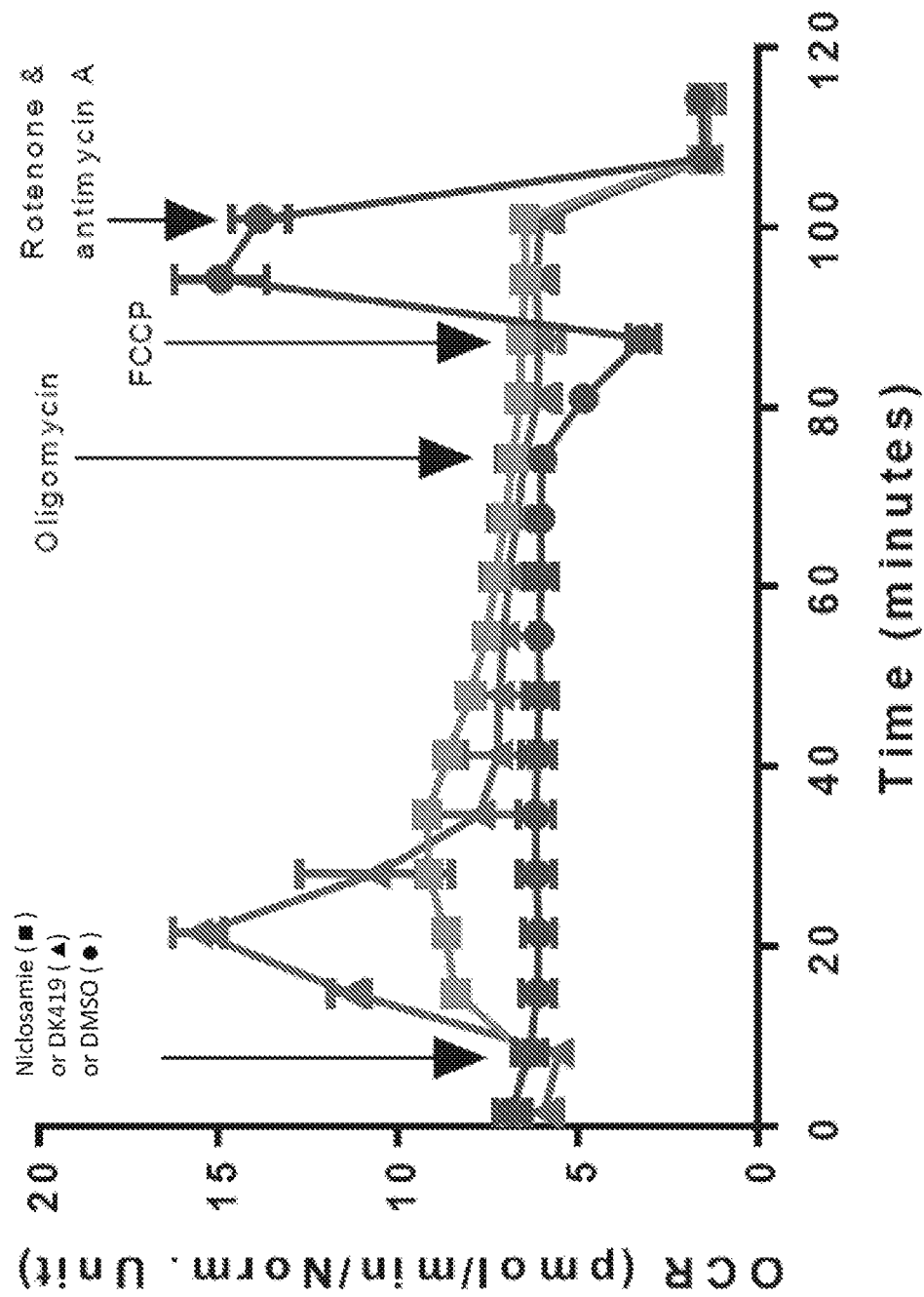
FIGS. 3A-3B show that DK419 increases oxygen consumption rate and induces pAMPK in cell culture.
Figure 3B:
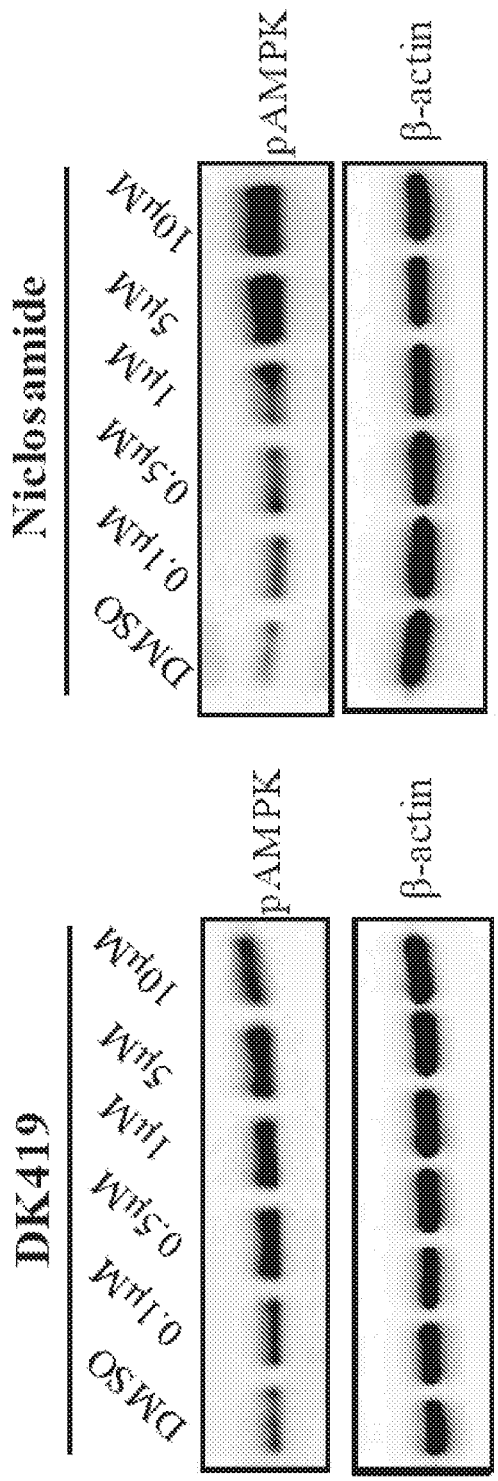

Increase in oxygen consumption rate and induction of pAMPK Niclosamide induces activating phosphorylation of AMPK and increases cellular oxygen consumption rate, both likely a result of its uncoupling of mitochondria oxidative phosphorylation. To determine if the molecular principles used in the design of DK419 were able to reproduce niclosamide's ability to uncouple oxidative phosphorylation and induce AMPK phosphorylation, DK419 and niclosamide were compared for their abilities to increase the oxygen consumption rate and induce phosphorylation of AMPK in CCD841Co cells, a normal epithelial colonic cell line (FIGS. 3A-3B). To assess the change in oxygen consumption rate, cells were treated with DK419 or niclosamide at 1 µM and oxygen consumption was compared versus DMSO control media using a Seahorse XFp analyzer (FIG. 3A). At the end of the experiment, Oligomycin, FCCP, Rotenone and Antimycin A were added sequentially to assess mitochondria status. FCCP, in particular, uncouples oxidative phosphorylation and increases oxygen consumption rate, as witnessed by the increased rate of oxygen consumption in the presence of the ATP synthase inhibitor Antimycin A in the cells treated with DMSO control media. Niclosamide also increases the oxygen consumption rate, indicating its ability to uncouple of oxidative phosphorylation in these cells. Consistent with its molecular design, DK419 increases the rate of oxygen consumption, which indicates a molecule that uncouples oxidative phosphorylation. It was found that the kinetic profile and the magnitude of the uncoupling effect is different at the single doses of niclosamide and DK419 used. The reason for this difference is not known but may reflect a difference in potency between the two compounds or differences in cell or mitochondrial membrane permeability. Overall, both niclosamide and DK419 at 1 µM caused oxygen consumption to increase and then decrease over time. The data from this experiment is consistent with the ability of these compounds to inhibit the spare respiratory capacity of mitochondria as demonstrated by the finding that treated cells did not respond to the subsequent addition of FCCP. The effects observed were consistent with a report that niclosamide at similar concentrations (0.5 and 1.5 µM) caused oxygen consumption rate to increase in HCT116 cells for which later addition of FCCP caused no further increase in oxygen consumption rate (Senkowski et al., Mol. Cancer Ther. 2015, 14, 1504). As expected, addition of Rotenone and Antimycin A at the end of the experiment decreased oxygen consumption, indicating that the mitochondria of cells treated with the uncoupling agent were still actively respiring.

To assess the ability of DK419 to induce phosphorylation of AMPK, CCD841Co cells were treated with DK419, niclosamide, or control media containing DMSO, and compared by Western blot (FIG. 3B). Niclosamide increased pAMPK levels versus control. Again, consistent with the molecular design, DK419 also increased the levels of pAMPK. Cellular levels of AMPK did not appear to change (data not shown). Taken together, these data indicate that DK419, like niclosamide, has effects on oxidative phosphorylation and impacts the levels of pAMPK.

Inhibition of colorectal cancer cell proliferation To assess the ability of DK419 to inhibit the proliferation of CRC tumor cell lines, the effect of DK419 and niclosamide on cell proliferation was evaluated using a MTS assay in six CRC tumor cell lines (Table 1). DK419 inhibited the proliferation of each of the Six CRC cell lines with $IC_{50}$ values ranging from 0.04 to 0.35 µM. Niclosamide also inhibited the proliferation of these cell lines, with $IC_{50}$ values that ranged from 0.1 to 1.78 µM. Overall, DK419 demonstrated the ability to inhibit the proliferation of CRC cells and showed a trend toward greater potency in these cell lines compared toniclosamide.

TABLE 1

Inhibition of cell proliferation by DK419 and niclosamide [a]

| Cell line | DK419 | Niclosamide |
| --- | --- | --- |
| SW948 | 0.04 | 0.10 |
| HT-29 | 0.11 | 0.10 |
| HCT116 | 0.23 | 0.31 |
| CRC240 | 0.31 | 0.68 |
| SW480 | 0.32 | 0.74 |
| DLD-1 | 0.35 | 1.78 |

[a] $IC_{50}$ values in µM from MTS assay at 72 hr.

Figure 4:
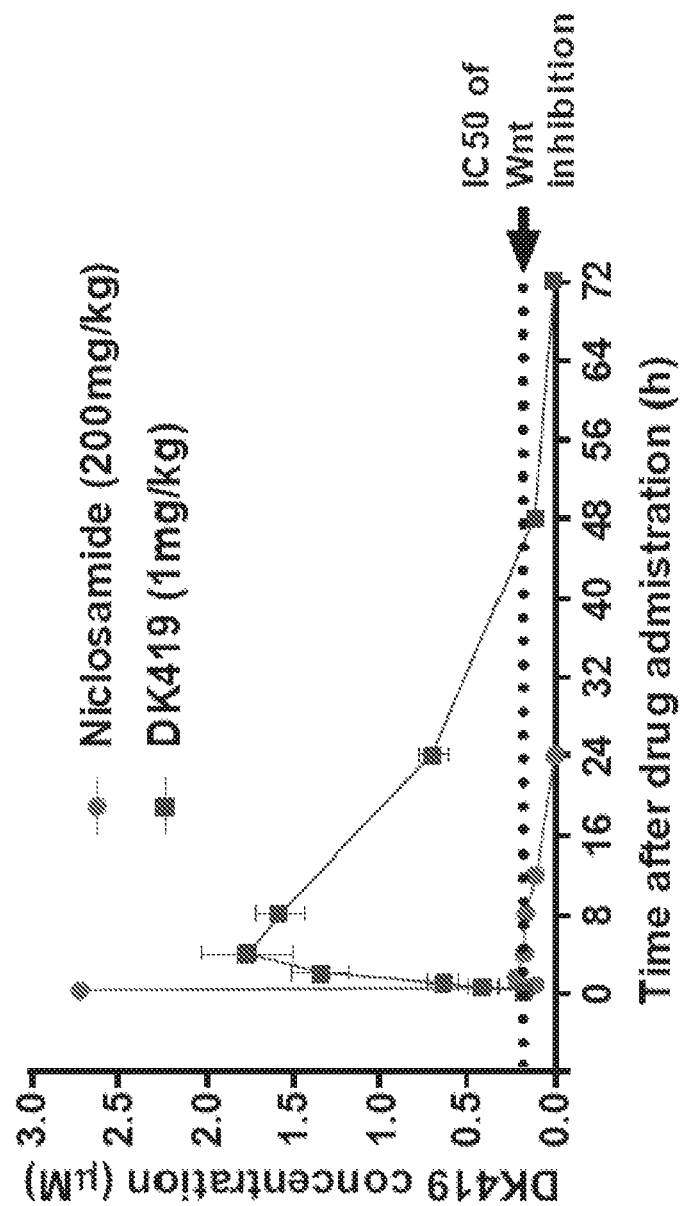
FIG. 4 shows representative plasma concentration of DK419 vs. time in mice. Adult mice were dosed orally with DK419 at 1 mg/kg of body weight. Blood samples were drawn serially at 0.25, 0.5, 1, 2, 4, 8, 24 h, 48, and 72 h after drug administration. N=4 per time point. Quantification of DK419 in mouse plasma was done by LC/MS-MS and reported as ng/ml. The data presented are mean±SEM. The dotted line is the $IC_{50}$ of DK419 inhibition of Wnt/β-catenin signaling in the TOPFlash assay. For comparison, the plasma concentration of niclosamideorally dosed at 200 mg/kg is also presented. Both DK419 and niclosamide were administered in the vehicle of 10% 1-methyl-2-pyrrolidinone and 90% PEG300 to NOD/SCID mice.

Systemic exposure from oral dose—plasma pharmacokinetics A central element in the design of DK419 was to identify Wnt/β-catenin inhibitors with improved oral exposure by tire removal of substituents in the structure of niclosamide that undergo metabolism and impact its absorption. In the case of DK419, the nitro group of niclosamide was replaced with a trifluoromethyl group and tire phenol replaced with an amine group within the benzimidazole ring system. To assess whether these design elements in DK419 offered improvements in systemic exposure from oral dosing, mice were dosed orally with DK419 at 1 mg/kg and the plasma concentration of DK419 evaluated over 72 hours (FIG. 4). Remarkably and unexpectedly, DK419 produced significantly higher levels of the inhibitor in plasma that were sustained for more than 24 hours. Namely, at this dose, the plasma concentration of DK419 at 24 hours was 3-fold higher than its $IC_{50}$ for inhibition of Wnt/β-catenin signaling and CRC proliferation in the TOPFlash and MTS assays. Overall, a single 1 mg/kg oral dose of DK419 produced much higher and more sustained systemic exposure than in case of a single 200 mg/kg oral dose of niclosamide (AUC/DOSE and $t_{1/2}$ values, Table 2), demonstrating that the design strategy herein resulted in much-improved pharmacokinetic properties of the new compound.

TABLE 2

Pharmacokinetic parameters. [a]

| PK Parameter | DK419 compartmental 1st order extrav. input, 1st order elimination | SEM | DK419 non-compartmental extravascular input | SEM | Niclosamide [b] non-compartmental extravascular input |
| --- | --- | --- | --- | --- | --- |
| DOSE, mg (per kg BW) | 1 | | 1 | | 200 |
| $T_{max}$, h | 5.85 | 0.52 | 4.5 | 0.51 | 0.25 |
| $C_{max}$, µM | 0.73 | 0.04 | 0.75 | 0.09 | 0.89 |
| $C_{max}$, µM | 1.79 | 0.09 | 1.84 | 0.23 | 2.73 |
| $AUC_{inf}$ h µg/mL (per kg BW) | 16.3 | 1.8 | 16.9 | 1.4 | 1.02 |

TABLE 2-continued

Pharmacokinetic parameters.[a]

| PK Parameter | DK419 compartmental 1st order extrav. input, 1st order elimination | SEM | DK419 non-compartmental extravascular input | SEM | Niclosamide[b] non-compartmental extravascular input |
|---|---|---|---|---|---|
| $AUC_{inf}$/DOSE, h µg/mL (per mg) | 16.3 | 1.8 | 16.9 | 1.4 | 0.005 |
| $AUC_{0-LAST}$ h µg/mL (per kg BW) | — | — | 16.8 (0-72 h) | 1.4 ( 0-24 h) | 1.01 |
| $t_{1/2}$-elimination, h , | 10.8 | 2.1 | 9.2 | 0.2 | 3.1 |
| $t_{1/2}$-absorption, h | 2.0 | 0.4 | — | — | — |
| $V_d$/F, L (per kg BW) | 0.98 | 0.12 | 0.80 (Vz) | 0.07 | 0.90 (Vz) |
| CL/F, L/h (per kg BW) | 0.06 | 0.007 | 0.06 | 0.004 | 0.20 |
| MRT, h | — | — | 15.8 | 0.9 | 6.8 |

[a] Both compartmental and non-compartmental modeling (WinNonlin) of DK419 plasma concentration-time data (FIG. 4) was performed.
[b] For comparison reported Niclosamide PK parameters (Osada et al. Cancer Research 2011, 71, 4172.) are included. Animal experiment and dosing conditions are as described in FIG. 4.

Figure 5B:
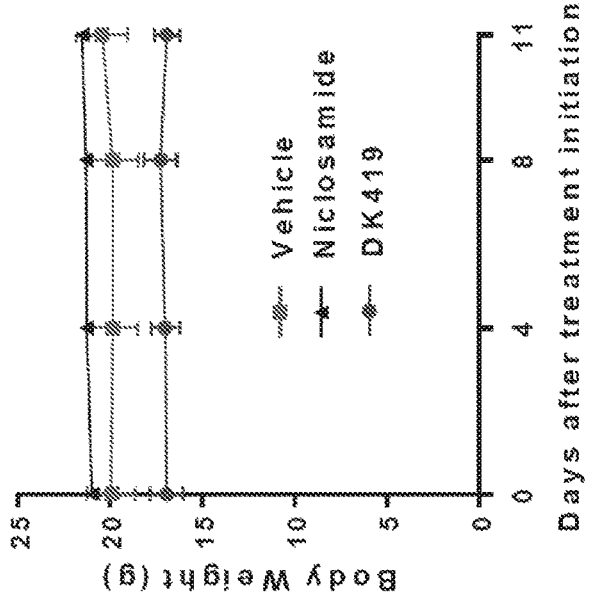
FIGS. 5A-5D shows representative results of in vivo inhibition of tumor growth by DK419 in mouse CRC240 PDX tumor model, NOD/SCID mice bearing CRC240 PDX tumors were dosed orally daily for 11 days with vehicle control, niclosamideat 72 mg/kg, or DK419 at 1 mg/kg. Tumor size and body weight were measured at day 0, 4, 8, and 11.
Figure 5A:
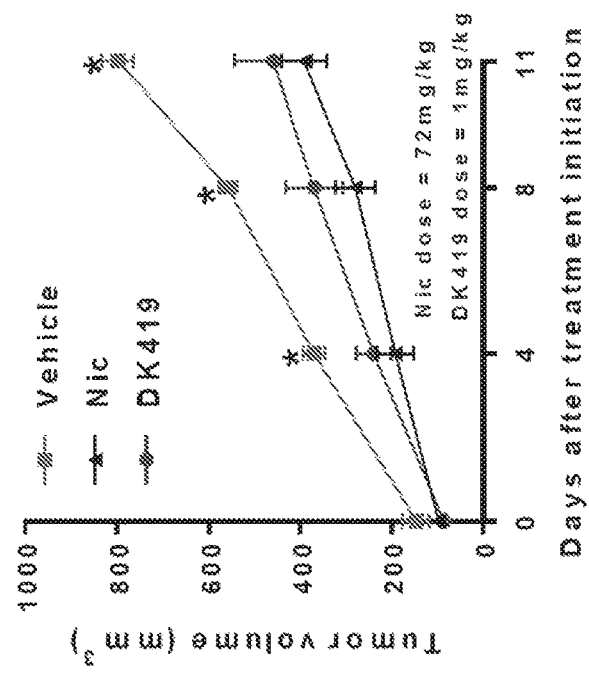
Figure 5C:
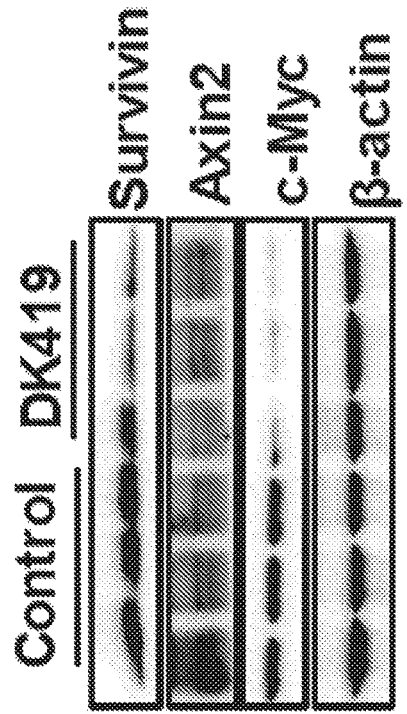
Figure 5D:
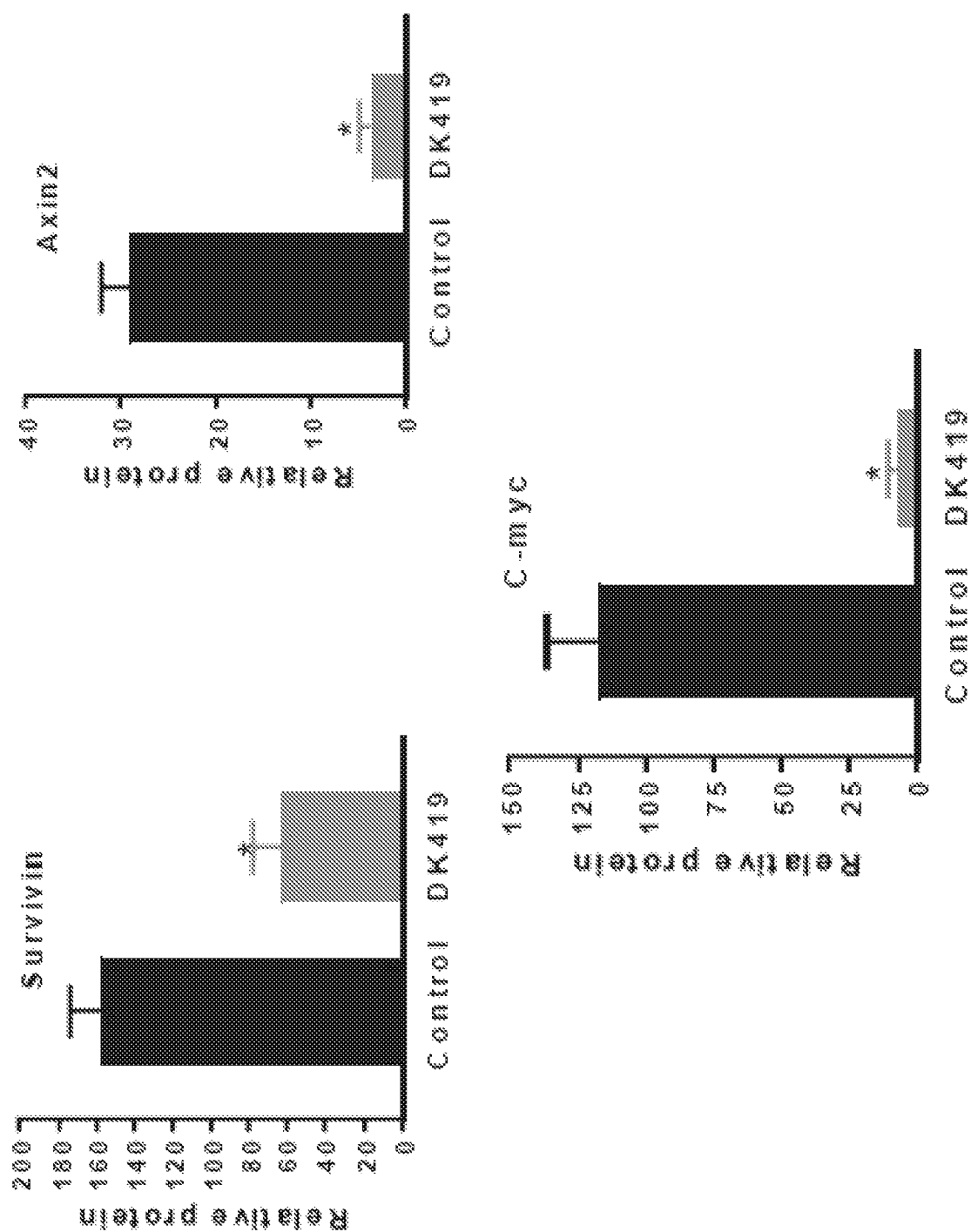

Inhibition of CRC tumor growth in vivo To assess the ability of DK419 to inhibit the growth of CRC tumors in vivo, DK419 was evaluated in a patient-derived tumor mouse xenograft model. In this model, NOD/SCID mice bearing CRC240 PDX tumors were dosed orally once a day with DK419 at 1 mg/kg (2.4 µmol/kg), niclosamide at 72 mg/kg (220 µmol/kg), or vehicle. Tumor volume and body weight were measured over the study. At the conclusion of the study, tumors were collected and analyzed for Wnt target gene protein levels (Axin2, Survivin and c-Myc). As shown in FIG. 5A, DK419 inhibited the growth of CRC240 PDX tumors compared to vehicle control. When compared against mice treated with niclosamide, DK419 at 1/90$^{th}$ the molar dose inhibited tumor growth to a similar level as niclosamide. Neither DK419 nor niclosamide produced a change in body weight (FIG. 5B). Moreover, in DK419 treated animals, the levels of each of the Wnt/β-catenin target genes in tumors were reduced significantly (FIGS. 5C and 5D). Overall, these studies demonstrate that DK419 can inhibit Wnt/β-catenin signaling and inhibit the growth of CRC tumors in vivo in a patient-derived CRC tumor model. Consistent with the pharmacokinetic studies indicating improved systemic exposure, DK419 demonstrated similar antitumor activity as niclosamide but at a significantly lower dose.

DISCUSSION

A design of a novel inhibitor of Wnt/β-catenin signaling based on the structure and SAR of niclosamide is described. In particular, the design aims to remove substituents in niclosamide's structure thought to contribute to its poor systemic exposure upon oral dosing. The design replaces the nitro and phenol substituents in niclosamide. This is the first example of a niclosamide derivative in winch the phenol can be replaced without a significant loss of Wnt/β-catenin inhibitor activity. In vitro, DK419 showed similar potency to niclosamide in the Fzd1-GFP internalization assay and in the Wnt3A-stimulated TOPFlash reporter assay. In multiple CRC cell lines that harbor mutations in the Wnt signaling pathway, DK419 reduced the levels of Wnt/β-catenin target gene proteins consistent with the results from the internalization and reporter assays. DK419 also inhibited the growth of multiple CRC cell lines in culture. In vivo, DK419 has good oral exposure in mice, producing plasma concentrations of DK4I9 24 hours after a single 1 mg/kg oral dose that are above its in vitro $IC_{50}$ values in the Wnt3A TOPFlash and the CRC cell proliferation assays. Tire exposure of DK419 at 1 mg/kg significantly exceeds the exposure of niclosamide at a dose of 200 mg/kg. Consistent with pharmacokinetic studies that show improved exposure, DK419 at a significantly lower dose inhibited the growth of tumors comparable to niclosamide in a human patient-derived colorectal PDX xenograft model and without effects on mouse body weight.

The biological target that binds to DK419 and niclosamide that results in inhibition of Wnt/β-catenin signaling is not known. This fact is due to the reverse chemical genetic screening method used in which the screening assay measures a functional output and not activity against a specific target. As a result, subsequent deconvolution may be carried out to identify the binding target. Niclosamide was initially identified from a high-throughput assay that screened for agents that induce internalization of the Frizzled receptor. Subsequent in vitro studies found that niclosamide decreased cellular levels of Dvl and cytosolic β-catenin, decreased levels of Wnt/β-catenin target gene proteins, and inhibited the proliferation of CRC cells in culture. In vivo, niclosamide inhibited the growth of CRC tumors in mouse models and reduced the levels of Wnt/β-catenin target proteins in tire CRC tumors even though its systemic exposure was generally low. Being designed from niclosamide and incorporating key SAR features, DK419 has a similar Wnt/β-catenin and CRC cell proliferation inhibitor profile, yet represents a significant advance due to its improved systemic exposure. The low exposure of niclosamide in humans is considered a risk to its success in multiple ongoing clinical trials. DK419 provides a framework to optimize its activity within a chemotype that demonstrates better exposure.

Initial SAR studies suggested that inhibition of Wnt signaling may be separate from the mechanism, associated with its anthelmintic activity, namely uncoupling of oxidative phosphorylation. Additional SAR studies demonstrated the ability to separate the two effects. Although the SAR suggests differences, there are also close similarities such that there may m fact be a relationship at some level between Wnt signaling and mitochondrial status. It is well known that Wnt and mitochondrial function are both critical for cancer growth and metastasis. Mitochondria in cancer cells are often compromised, and a growing body of literature demonstrates uncoupling mitochondrial oxidative phosphorylation can overcome resistance to anticancer drugs. Thus, the multifunctional activity of DK419 may have additional benefits in the treatment of cancer.

Using the SAR of niclosamide, compounds (such as DK419) were identified as novel inhibitors of Wnt/β-catenin signaling that mimics niclosamide's inhibition of Wnt/β-catenin signaling and uncoupling of oxidative phosphorylation. The compounds also overcome niclosamide's poor exposure when dosed orally. DK419 represents a new chemotype of Wnt/β-catenin inhibitors. Accordingly, DK419 may be used as an agent to treat cancers and other Wnt-related diseases, as well as diseases in which niclosamide has demonstrated important medicinal activity.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to tire chemical structures, substituents, derivatives, intermediates, syntheses, compositions, formulations, or methods of use of the invention, may be made without departing from the spirit and scope thereof.

What is claimed is:

1. A compound of formula (I), or a pharmaceutically acceptable salt thereof,

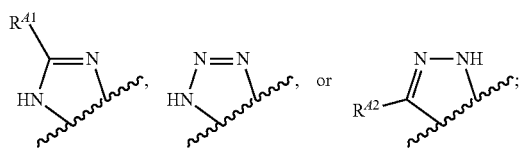

(I)

wherein, is

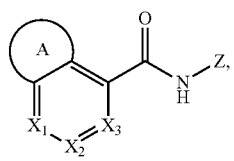

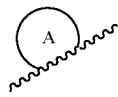

$X_1$ is N or $CR^{x1}$;
$X_2$ is N;
$X_3$ is N or $CR^{x3}$;
Z is aryl or heteroaryl, wherein the aryl and the heteroaryl are optionally substituted with 1, 2, 3, or 4 $R^Z$;
$R^{41}$ and $R^{42}$ are haloalkyl, halogen, oxo, cyano, nitro, —OH, alkoxy, or —C(O)alkyl;

$R^{x1}$ and $R^{x3}$ are independently selected from the group consisting of hydrogen, halogen, nitro, alkyl, cyano, haloalkyl, alkoxyalkyl, heteroalkyl, alkenyl, alkynyl, heterocycle, carboxyl, heterocyclealkyl, —OH, alkoxy, —$OR^4$, —$SR^5$, —$NR^6R^7$, and —$NR^8$—$SO_2$—$R^9$;

$R^Z$ at each occurrence is independently selected from the group consisting of halogen, nitro, alkyl, cyano, haloalkyl, alkoxyalkyl, heteroalkyl, alkenyl, alkynyl, heterocycle, carboxyl, heterocyclealkyl, —OH, alkoxy, —$OR^4$, —$SR^5$, —$NR^6R^7$, —$SO_2$—$R^9$, and —$NR^8$—$SO_2$—$R^9$;

$R^4$ is selected from —C(O)-alkyl, —C(O)-alkenyl, —C(O)-heteroalkyl, —C(O)-heteroaryl, —C(O)-alkoxyalkyl, —C(O)—O-heteroalkyl, —C(O)—O-heteroaryl, —C(O)—O-alkyl, —C(O)—O-alkenyl, and —C(O)—O— alkoxyalkyl;

$R^5$, $R^6$ and $R^7$ are each independently selected from hydrogen, alkyl, —C(O)-alkyl, —C(O)—O-alkyl, —C(O)—O-alkenyl, —C(O)-alkoxyalkyl, —C(O)—NH-alkyl, —C(O)-heterocycle, -alkenyl, alkynyl, and heteroalkyl;

$R^8$ is selected from hydrogen and alkyl; and $R^9$ is selected from hydrogen, alkyl, aryl, heteroaryl, arylalkyl, heterocycle and heteroarylalkyl, provided that Z is not benzo[d]thiazole or substituted benzo[d]thiazole.

2. The compound of claim 1, or a pharmaceutically acceptable salt thereof, wherein

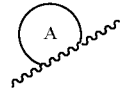

is

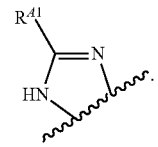

3. The compound of claim 1, or a pharmaceutically acceptable salt thereof, wherein $X_1$ is $CR^{x1}$ and $X_3$ is $CR^{x3}$.

4. The compound of claim 1, or a pharmaceutically acceptable salt thereof, wherein one of $X_1$ and $X_3$.

5. The compound of claim 1, or a pharmaceutically acceptable salt thereof, wherein $R^{41}$ is $C_{1-4}$ haloalkyl.

6. The compound of any claim 1, or a pharmaceutically acceptable salt thereof, wherein $R^{41}$ is —$CF_3$.

7. The compound of claim 1, or a pharmaceutically acceptable salt thereof, wherein Z is a phenyl optionally substituted with 1, 2, 3, or 4 $R^Z$.

8. The compound of claim 1, or a pharmaceutically acceptable salt thereof, wherein Z is

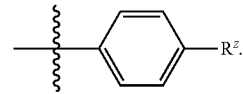

9. The compound of claim 8, or a pharmaceutically acceptable salt thereof, wherein $R^z$ is $C_{1-4}$alkyl, $C_{1-4}$haloalkyl, $C_{1-4}$alkoxy, halogen, cyano, or nitro.

10. The compound of claim 9, or a pharmaceutically acceptable salt thereof, wherein $R^z$ is —$CF_3$.

11. The compound of claim 1, or a pharmaceutically acceptable salt thereof, wherein Z is a monocyclic heteroaryl or a bicyclic heteroaryl.

12. The compound of claim 1, wherein the compound of formula (I) is or a pharmaceutically acceptable salt thereof.

13. A pharmaceutical composition comprising a compound of claim 1, or a pharmaceutically acceptable salt there, and a pharmaceutically acceptable carrier.

14. A method of treating a disease associated with dysregulation of the Wnt/Frizzled signaling pathway in a subject in need thereof, the method comprising
administering to the subject an effective amount of a compound of formula (I'), or a pharmaceutically acceptable salt thereof, (I')

wherein, is $X_1$ is N or $CR^{x1}$;
$X_2$ is N;
$X_3$ is N or $CR^{x3}$;
Z is aryl or heteroaryl, wherein the aryl and the heteroaryl are optionally substituted with 1, 2, 3, or 4 $R^z$;
$R^{41}$ and $R^{42}$ are haloalkyl, halogen, oxo, cyano, nitro, —OH, alkoxy, or —C(O)alkyl;
$R^{x1}$ and $R^{x3}$ are independently selected from the group consisting of hydrogen, halogen, nitro, alkyl, cyano, haloalkyl, alkoxyalkyl, heteroalkyl, alkenyl, alkynyl, heterocycle, carboxyl, heterocyclealkyl, —OH, alkoxy, —$OR^4$, —SR, —$NR^6R^7$, and —$NR^8$—$SO_2$—$R^9$;

$R^z$ at each occurrence is independently selected from the group consisting of halogen, nitro, alkyl, cyano, haloalkyl, alkoxyalkyl, heteroalkyl, alkenyl, alkynyl, heterocycle, carboxyl, heterocyclealkyl, —OH, alkoxy, —$OR^4$, —$SR^5$, —$NR^6R^7$, —$SO_2$—$R^9$, and —$NR^9$—$SO_2$—$R^9$;

$R^4$ is selected from —C(O)-alkyl, —C(O)-alkenyl, —C(O)-heteroalkyl, —C(O)-heteroaryl, —C(O)-alkoxyalkyl, —C(O)—O-heteroalkyl, —C(O)—O-heteroaryl, —C(O)—O-alkyl, —C(O)—O-alkenyl, and —C(O)—O— alkoxyalkyl;

$R^5$, $R^1$ and $R^7$ are each independently selected from hydrogen, alkyl, —C(O)-alkyl, —C(O)—O-alkyl, —C(O)—O-alkenyl, —C(O)-alkoxyalkyl, —C(O)—NH-alkyl, —C(O)-heterocycle, -alkenyl, alkynyl, and heteroalkyl;

$R^8$ is selected from hydrogen and alkyl; and $R^9$ is selected from hydrogen, alkyl, aryl, heteroaryl, arylalkyl, heterocycle and heteroarylalkyl.

15. The method of claim 14, wherein the disease is selected from the group consisting of cancer, fatty liver, antibiotic resistance, bacterial infection, viral infection, diabetes, fibrotic disease, and primary sclerosing cholangitis.

16. The method of claim 14, wherein the compound of formula (I) is or a pharmaceutically acceptable salt thereof.

17. A method of modulating the Wnt/Frizzled signaling pathway in a subject, the method comprising
administering to the subject an effective amount of a compound of formula (I'), or a pharmaceutically acceptable salt thereof, (I')

wherein, is

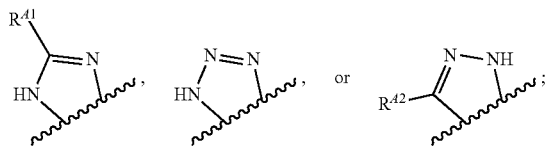

X₁ is N or CR$^{x1}$;
X₂ is N;
X₃ is N or CR$^{x3}$;
Z is aryl or heteroaryl, wherein the aryl and the heteroaryl are optionally substituted with 1, 2, 3, or 4 R$^z$;
R$^{41}$ and R$^{42}$ are haloalkyl, halogen, oxo, cyano, nitro, —OH, alkoxy, or —C(O)alkyl;
R$^{x1}$ and R$^{x3}$ are independently selected from the group consisting of hydrogen, halogen, nitro, alkyl, cyano, haloalkyl, alkoxyalkyl, heteroalkyl, alkenyl, alkynyl, heterocycle, carboxyl, heterocyclealkyl, —OH, alkoxy, —OR$^4$, —SRS, —NR R$^7$, and —NR$^8$—SO₂—R$^9$;
R$^z$ at each occurrence is independently selected from the group consisting of halogen, nitro, alkyl, cyano, haloalkyl, alkoxyalkyl, heteroalkyl, alkenyl, alkynyl, heterocycle, carboxyl, heterocyclealkyl, —OH, alkoxy, —OR$^4$, —SR$^1$, —NR$^6$R$^7$, —SO₂—R$^9$, and —NR$^8$—SO₂—R$^9$;
R$^4$ is selected from —C(O)-alkyl, —C(O)-alkenyl, —C(O)-heteroalkyl, —C(O)-heteroaryl, —C(O)—alkoxyalkyl, —C(O)—O-heteroalkyl, —C(O)—O-heteroaryl, —C(O)—O-alkyl, —C(O)—O-alkenyl, and —C(O)—O— alkoxyalkyl;
R$^5$, R$^6$ and R$^7$ are each independently selected from hydrogen, alkyl, —C(O)-alkyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl;
R$^8$ is selected from hydrogen and alkyl; and
R$^9$ is selected from hydrogen, alkyl, aryl, heteroaryl, arylalkyl, heterocycle and heteroarylalkyl.

18. The method of claim 14, wherein

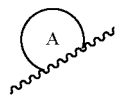

is

19. The method of claim 17, wherein

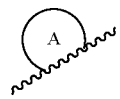

is

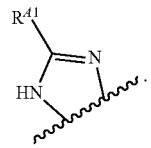

20. The method of claim 17, wherein the compound of formula (I') is:

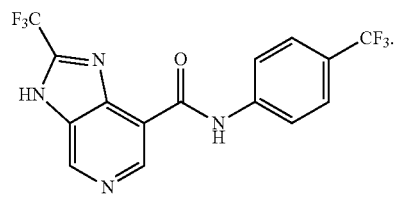 [SMILES: O=C(Nc1ccc(C(F)(F)F)cc1)c1cncc2[nH]c(C(F)(F)F)nc12]

or a pharmaceutically acceptable salt thereof.

* * * * *